United States Patent

Kawashima et al.

[11] Patent Number: 5,872,281
[45] Date of Patent: Feb. 16, 1999

[54] AMINO ACID DERIVATIVE HAVING N,N-DIALKYLAMINOPHENYL GROUP

[75] Inventors: Yoichi Kawashima, Kyoto; Masato Horiuchi, Settsu, both of Japan

[73] Assignee: Santen Pharmaceutical Co., Ltd., Osaka, Japan

[21] Appl. No.: 913,093

[22] PCT Filed: Mar. 5, 1996

[86] PCT No.: PCT/JP96/00521

§ 371 Date: Sep. 5, 1997

§ 102(e) Date: Sep. 5, 1997

[87] PCT Pub. No.: WO96/27585

PCT Pub. Date: Sep. 12, 1996

[30] Foreign Application Priority Data

Mar. 7, 1995 [JP] Japan .................. 7-046816

[51] Int. Cl.$^6$ .............. C07C 229/00; C07C 303/00; C07C 261/00
[52] U.S. Cl. ............ 562/433; 562/457; 562/621; 560/13; 560/24; 560/43
[58] Field of Search .................. 562/433, 457, 562/621; 560/13, 24, 43

[56] References Cited

U.S. PATENT DOCUMENTS 4,362,738 12/1982 Keck et al. .............. 514/418
5,061,710 10/1991 Haslanger et al. .
5,292,926 3/1994 Morita et al. .

FOREIGN PATENT DOCUMENTS 2-776 1/1990 Japan .
2-503799 11/1990 Japan .

OTHER PUBLICATIONS

Database Caplus, No. 95:61792, DE 2926471 Krueger et al., 'Aminobenzoic acid derivatives for use as pharmaceuticals or intermediatee products.' abstracts, Nov. 15, 1981.

*Primary Examiner*—Gary Geist
*Assistant Examiner*—Brian J. Davis
*Attorney, Agent, or Firm*—Frishauf, Holtz, Goodman, Langer & Chick, P.C.

[57] ABSTRACT

A compound of the formula

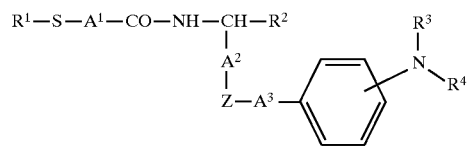

wherein $R^1$ is hydrogen, lower alkyl, phenyl-lower alkyl, lower alkanoyl or benzoyl, and each phenyl in the phenyl-lower alkyl and the benzoyl is unsubstituted or substituted by halogen, lower alkyl or alkoxy; $R^2$ represents a carboxyl or a carboxyl which is converted into an ester, an amide or a hydroxamic acid; $R^3$ represent a lower alkyl; $R^4$ represents a lower alkyl; $A^1$ represents a lower alkylene which is unsubstituted or substituted by a phenyl and the phenyl is unsubstituted or substituted by halogen, lower alkyl or a lower alkoxy; $A^2$ represents a lower alkylene; $A^3$ represents a lower alkylene; and Z represents a sulfur or an oxygen. The compounds have inhibitory effects on $LTA_4$ hydrolase and are useful for treating rheumatic diseases, psoriasis, inflammatory intestinal diseases, gout and cystic fibrosis.

33 Claims, No Drawings

AMINO ACID DERIVATIVE HAVING N,N-DIALKYLAMINOPHENYL GROUP

TECHNICAL FIELD

The present invention relates to a sulfur or oxygen-containing amino acid derivative in which an N,N-dialkylaminophenyl group is introduced into a side chain, and which has inhibitory activity on leukotriene $A_4$ hydrolase, and is useful as a medicine such as an agent for treating inflammatory diseases such as rheumatic diseases, psoriasis, inflammatory intestinal diseases, gout and cystic fibrosis.

BACKGROUND TECHNIQUES

Leukotriene $A_4$ (hereinafter, abbreviated as $LTA_4$) hydrolase, which is one of the epoxide hydrolase, is a metal-containing enzyme which requires zinc in an active center.

$LTA_4$ hydrolase plays a catalyst-like role on biochemical conversion from $LTA_4$ into leukotriene $B_4$ (hereinafter, abbreviated as $LTB_4$), which is a strong pro-inflammatory substance.

$LTB_4$ is arachidonic acid metabolite which is produced in 5-lipoxygenase pathway, biosynthesized in various cells including mast cell, neutrophil, monocyte, macrophage and the like, and plays a role as an important mediator in inflammation. $LTB_4$ induces chemotaxis, coagulation and degranulation of leukocyte and accumulation of polymorphonuclear leukocyte, and accelerates blood vessel permeability and edema formation. For this reason, it was reported that particularly high level of $LTB_4$ was detected in lesion parts in inflammatory diseases such as rheumatic diseases (J. Clin. Invest., 66, 116–117 (1980)), psoriasis (Br. J. Pharmacol., 83, 313–317 (1984)), inflammatory bowel diseases (Gastroenterology, 86, 453–460 (1984)) and gout (Lancet, 2, 1122–1124 (1982)) and in sputum in cystic fibrosis (Lancet, 342, 465–469 (1993)).

Therefore, compounds which inhibit $LTA_4$ hydrolase are expected to prevent production of $LTB_4$ and manifest therapeutic effects on inflammatory diseases.

3-Oxiranyl benzoic acid and a derivative thereof were reported to have $LTA_4$ hydrolase inhibitory activity and be useful as an agent for treating inflammatory diseases such as psoriasis, inflammatory intestinal diseases, arthritis and gout (JP-A 2-134375).

In addition, (+)-1-(3S, 4R)-[3-(4-phenylbenzyl)-4-hydroxychroman-7-yl]cyclopentanecarboxylic acid was reported to have $LTA_4$ hydrolase inhibitory activity and inhibit sideration of arthritis in a collagen-induced arthritis model (J. Med. Chem., 37, 3197–3199 (1994)).

On the other hand, the structural features of the present invention is in amino acid having a sulfur or oxygen atom in which the sulfur or oxygen atom is bonded with (N,N-dialkylaminophenyl)alkyl, and an amino group is bonded to a sulfur-containing acyl group. From a viewpoint of the chemical structure, the prior art will be described below.

Compounds in which a phenyl group is introduced on a side chain of a sulfur-containing amino acid derivative was reported to be useful as a therapeutic agent for rheumatoid diseases and a hypotensive agent (JP-A 61-165362), because the compounds have rheumatoid factor's inactivating activity and angiotensin converting enzyme inhibitory activity, and also have endopeptidase 24.11 inhibitory activity (J. Med. Chem., 37, 2461–2476 (1994). However, a phenyl ring in amino acid side chain in the compounds described in these reports is not substituted and, thus, there is no description on compounds in which a substituent is introduced in a phenyl ring.

As described above, although various studies were done on sulfur-containing amino acid derivatives having a non-substituted phenyl ring on a side chain, no study has been done yet on sulfur-containing and oxygen-containing amino acid derivatives in which an N,N-dialkylamino group is introduced on its phenyl ring. Thus, a study regarding synthesis of the above compounds and a study regarding their pharmacological activities, particularly, activities on $LTA_4$ hydrolase were very interesting themes.

DISCLOSURE OF THE INVENTION

The present inventors aimed at a phenyl ring on a side chain of an amino acid derivative, and performed synthesis of compounds represented by the general formula [I] which are novel amino acid derivatives with an N,N-dialkylamino group introduced on the phenyl ring and salts thereof (hereinafter, referred to as the present compound), and studied the pharmacological activity thereof. A study was made using $LTA_4$ which is a substrate for $LTA_4$ hydrolase and using as an index an amount of $LTB_4$ produced by an enzymatic reaction and, as a result, it was found that the present compound has strong inhibitory activity on $LTA_4$ hydrolase. The present compound is expected to be useful as a medicine, particularly, an agent for treating inflammatory diseases such as rheumatic diseases, psoriasis, inflammatory intestinal diseases, gout and cystic fibrosis.

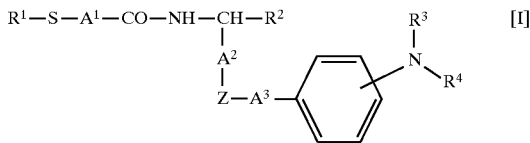

wherein $R^1$ represents a hydrogen atom, a lower alkyl group, a phenyl-lower alkyl group, a lower alkanoyl group or a benzoyl group, each phenyl ring in the phenyl-lower alkyl group and the benzoyl group can be substituted by a halogen atom, a lower alkyl group or a lower alkoxy group, $R^2$ represents a carboxyl group which can optionally be converted into an ester, an amide or a hydroxamic acid, $R^3$ represents a lower alkyl group, $R^4$ represents a lower alkyl group, $A^1$ represents a lower alkylene group optionally substituted by a phenyl group, the phenyl group can be substituted by a halogen atom, a lower alkyl group or a lower alkoxy group, $A^2$ represents a lower alkylene group, $A^3$ represents a lower alkylene group, and "Z" represents a sulfur atom or an oxygen atom, the same definitions of substituents will be used hereinafter.

The above defined groups will be described in detail. Halogen atom refers to fluorine, chlorine, bromine and iodine. Lower alkyl refers to straight or branched alkyls having 1 to 6 carbon atoms such as methyl, ethyl, propyl, hexyl, isopropyl and tert-butyl. Lower alkanoyl refers to straight or branched alkanoyls having 2 to 6 carbon atoms such as acetyl, propionyl, butyryl, hexanoyl, isobutyryl and pivaloyl. Lower alkoxy refers to straight or branched alkoxys having 1 to 6 carbon atoms such as methoxy, ethoxy, propoxy, butoxy, hexyloxy, isopropoxy and tert-butoxy. Lower alkylene refers to straight or branched alkylenes having 1 to 6 carbon atoms such as methylene, ethylene, trimethylene, tetramethylene, pentamethylene, hexamethylene, methylmethylene, propylene, ethylethylene, dimethylethylene, propylethylene, isopropylethylene and methyltrimethylene.

Ester refers to esters which are widely used as a carboxylic ester, such as a lower alkyl ester such as a methyl ester, an ethyl ester, a hexyl ester, an isopropyl ester or a tert-butyl ester, and a phenyl-lower alkyl ester such as a benzyl ester. Amide refers to amides which are used as an amide of a carboxylic acid, such as an amide with ammonia, amides with a tower alkyl amine such as methylamine, dimethylamine or ethylamine, and an amide with a phenyl-lower alkylamine such as benzyl amine, Salts in the present compound refer to any salts which are pharmaceutically acceptable and examples thereof are salts with an inorganic acid such as hydrochloric acid, nitric acid or sulfuric acid, salts with an alkali metal and alkaline earth metal such as sodium, potassium or calcium, ammonium salt, and salts with an organic amine such as diethylamine or triethanolamine. In addition, the present compound may be in the hydrate form.

By the way, in compounds applied to a medicine, the techniques are used in which compounds are converted into prodrugs such as esterification of carboxylic acid and the like for the purpose of promoting absorption and improving duration in the living body and stabilizing pharmaceutical preparations, and those derivatives are also used as preparation means, that is, as an synthetic intermediate. Therefore, also in the present invention, a carboxyl group can be converted into the form of an ester or an amide which is a conventional derivative of a carboxylic acid.

Among the present compounds, the following compounds are preferable examples.

Compound (a) wherein, in the above general formula [I], $R^1$ represents a hydrogen atom, a lower alkyl group, a phenyl-lower alkyl group, a lower alkanoyl group or a benzoyl group, each phenyl ring in the phenyl-lower alkyl group and the benzoyl group can be substituted by a halogen atom, a lower alkyl group or a lower alkoxy group, $R^2$ represents a carboxyl group which can be converted into a lower alkyl ester or a phenyl-lower alkyl ester; a carboxyl group which can be converted into an amide with ammonia, a lower alkyl amine or a phenyl-lower alkyl amine or a carboxyl group which can be converted into a hydroxamic acid; each phenyl ring in the phenyl-lower alkylester and the phenyl-lower alkylamine can be substituted by a halogen atom, a lower alkyl group, a hydroxyl group, a lower alkoxy group, a lower alkylenedioxy group, a nitro group, an amino group, a lower alkylamino group or a lower alkanoylamino group, $R^3$ and $R^4$ each represents a lower alkyl group, $A^1$ represents a lower alkylene group which can be substituted by a phenyl group, the phenyl group can be substituted by a halogen atom, a lower alkyl group or a lower alkoxy group, $A^2$ and $A^3$ each represents a lower alkylene group, and "Z" represents a sulfur atom or an oxygen atom, or salts thereof.

Among compound (a) and salts thereof, particular examples are as follows:

Compounds and salts thereof wherein $R^1$ represents a hydrogen atom, a lower alkyl group, a phenyl-lower alkyl group or a benzoyl group in compound (a).

Compounds and salts thereof wherein $R^1$ represents a hydrogen atom, a methyl group, a benzyl group or a benzoyl group in compound (a).

Compounds and salts thereof wherein $R^1$ represents a hydrogen in compound (a).

Compounds and salts thereof wherein $R^2$ represents a carboxyl group which can be converted into a lower alkyl ester or a phenyl-lower alkyl ester; or a carboxyl group which can be converted into an amide with a lower alkylamine or a phenyl-lower alkylamine in compound (a).

Compounds and salts thereof wherein $R^2$ represents a carboxyl group which can be converted into a lower alkyl ester; or a carboxyl group which can be converted into an amide with a lower alkylamine in compound (a).

Compounds and salts thereof wherein $R^2$ represents a carboxyl group which can be converted into an ethyl ester; or a carboxyl group which can be converted into an amide with methylamine in compound (a).

Compounds and salts thereof wherein $R^2$ represents a carboxyl group which can be converted into a lower alkyl ester in compound (a).

Compounds and salts thereof wherein $R^2$ represents a carboxyl group which can be converted into an ethyl ester in compound (a).

Compounds and salts thereof wherein $R^3$ and $R^4$ are the same or different and each represents a methyl group or an ethyl group in compound (a).

Compounds and salts thereof wherein $A^1$ represents a lower alkylene group which can be substituted by a phenyl group in compound (a).

Compounds and salts thereof wherein $A^1$ represents a methylene group, a methylmethylene group, an ethylene group, a propylene group, an ethylethylene group, a propylethylene group, an isopropylethylene group, a benzylethylene group, a phenethylethylene group, a trimethylene group or a methyltrimethylene group in compound (a).

Compounds and salts thereof wherein $A^1$ represents a methylene group, an ethylene group, a propylene group, an ethylethylene group, a propylethylene group, an isopropylethylene group or a phenethylethylene group in compound (a).

Compounds and salts thereof wherein "Z" represents a sulfur atom in compound (a).

Compounds and salts thereof wherein $R^1$ represents a hydrogen atom, a lower alkyl group, a phenyl-lower alkyl group or a benzoyl group, $R^2$ represents a carboxyl group which can be converted into a lower alkyl ester or a phenyl-lower alkyl ester; or a carboxyl group which can be converted into an amide with a lower alkylamine or a phenyl-lower alkylamine in compound (a).

Compounds and salts thereof wherein $R^1$ represents a hydrogen atom, a lower alkyl group, a phenyl-lower alkyl group or a benzoyl group, $R^2$ represents a carboxyl group which can be converted into a lower alkyl ester; or a carboxyl group which can be converted into an amide with a lower alkylamine in compound (a).

Compounds and salts thereof wherein $R^1$ represents a hydrogen atom, a methyl group, a benzyl group or a benzoyl group, $R^2$ represents a carboxyl group which can be converted into an ethyl ester; or a carboxyl group which can be converted into an amide with methylamine in compound (a).

Compounds and salts thereof wherein $R^1$ represents a hydrogen atom, $R^2$ represents a carboxyl group which can be converted into a lower alkyl ester, and "Z" represents a sulfur atom in compound (a).

Compounds and salts thereof wherein $R^1$ represents a hydrogen atom, $R^2$ represents a carboxyl group which can be converted into an ethyl ester, and "Z" represents a sulfur atom in compound (a).

Further, preferable examples of the present compound are as follows:

Compound (b) and salts thereof wherein $R^1$ represents a hydrogen atom, a lower alkyl group, a phenyl-lower alkyl group or a benzoyl group, $R^2$ represents a carboxyl group which can be converted into a lower alkyl ester or a phenyl-lower alkyl ester; or a carboxyl group which can be converted into an amide with a lower alkylamine or a phenyl-lower alkylamine, $R^3$ and $R^4$ each represents a lower alkyl group, $A^1$ represents a lower alkylene group which can be substituted by a phenyl group, $A^2$ and $A^3$ each represents a lower alkylene group, "Z" represents a sulfur atom or an oxygen atom in the above general formula [I].

Compound (c) and salts thereof wherein $R^1$ represents a hydrogen atom, a lower alkyl group, a phenyl-lower alkyl group or a benzoyl group, $R^2$ represents a carboxyl group which can be converted into a lower alkyl ester; or a carboxyl group which can be converted into an amide with a lower alkylamine, $R^3$ and $R^4$ each represents a lower alkyl group, $A^1$ represents a lower alkylene group which can be substituted by a phenyl group, $A^2$ and $A^3$ each represents a lower alkyene group, "Z" represents a sulfur atom or an oxygen atom in the above general formula [I].

Compounds and salts thereof wherein $R^1$ represents a hydrogen atom, a methyl group, a benzyl group or a benzoyl group, $R^2$ represents a carboxyl group which can be converted into an ethyl ester; or a carboxyl group which can be converted into an amide with methylamine, $R^3$ and $R^4$ are the same or different and each represents a methyl group or an ethyl group, $A^1$ represents a methylene group, a methylmethylene group, an ethylene group, a propylene group, an ethylethylene group, a propylethylene group, an isopropylethylene group, a benzylethylene group, a phenethylethylene group, a trimethylene group or a methyltrimethylene group, $A^2$ represents a methylene group or an ethylene group, and $A^3$ represents a methylene group in compound (c).

Compound (d) and salts thereof wherein $R^1$ represents a hydrogen atom, $R^2$ represents a carboxyl group which can be converted into a lower alkyl ester, $R^3$ and $R^4$ each represents a lower alkyl group, $A^1$ represents a lower alkylene group which can be substituted by a phenyl group, $A^2$ and $A^3$ each represents a lower alkylene group, and "Z" represents a sulfur atom in the above general formula [I].

Compounds and salts thereof wherein $R^2$ represents a carboxyl group which can be converted into an ethyl ester, $R^3$ represents a methyl group or an ethyl group, $R^4$ represents a methyl group or an ethyl group, $A^1$ represents a methylene group, an ethylene group, a propylene group, an ethylethylene group, a propylethylene group, an isopropylethylene group or a phenethylethylene group, $A^2$ and $A^3$ both represent a methylene group in compound (d).

As an embodiment of preferable compound of the present invention, there are 3-[4-(N,N-dimethylamino)benzylthio]-2-(3-mercapto-2-methylpropionylamino)propionic acid represented by the following formula [II] and salts, an optical isomer, a diastereomer thereof, for example, (2R)-3-[4-(N,N-dimethylamino)benzylthio]-2-[(2S)-3-mercapto-2-methylpropionylamino]propionic acid represented by the following formula [XIII], and further (2R)-3-[4-(N,N-dimethylamino)benzylthio]-2-[(2S)-3-mercapto-2-propylpropionylamino]propionic acid represented by the following formula [XIV], and salts thereof.

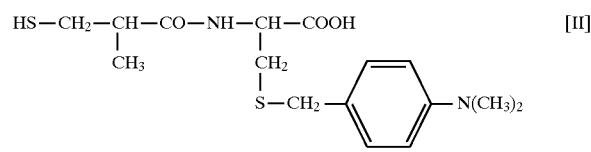

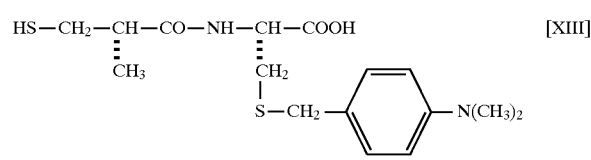

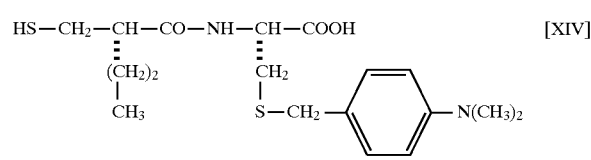

A representative process for synthesizing the present compound will be described below.

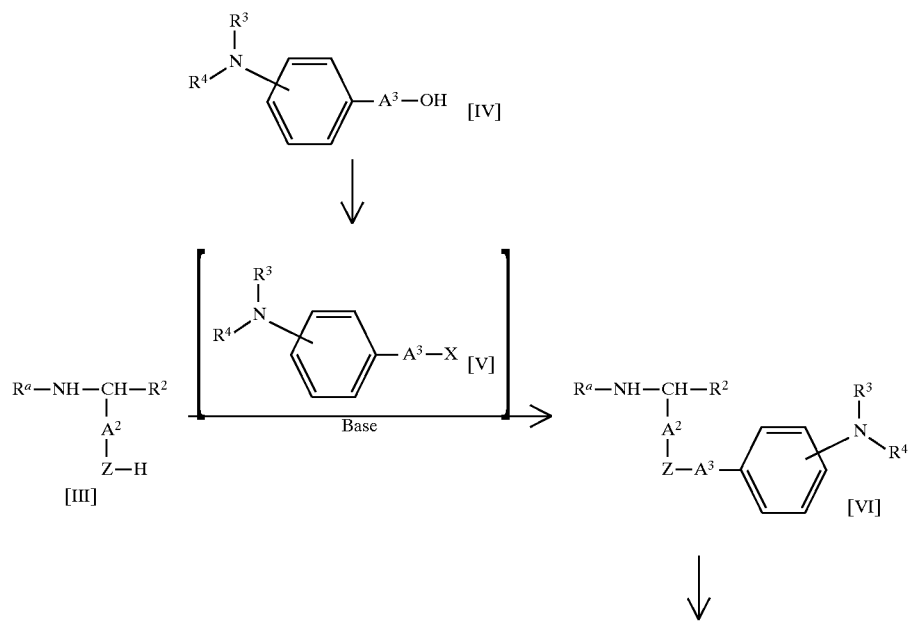

-continued

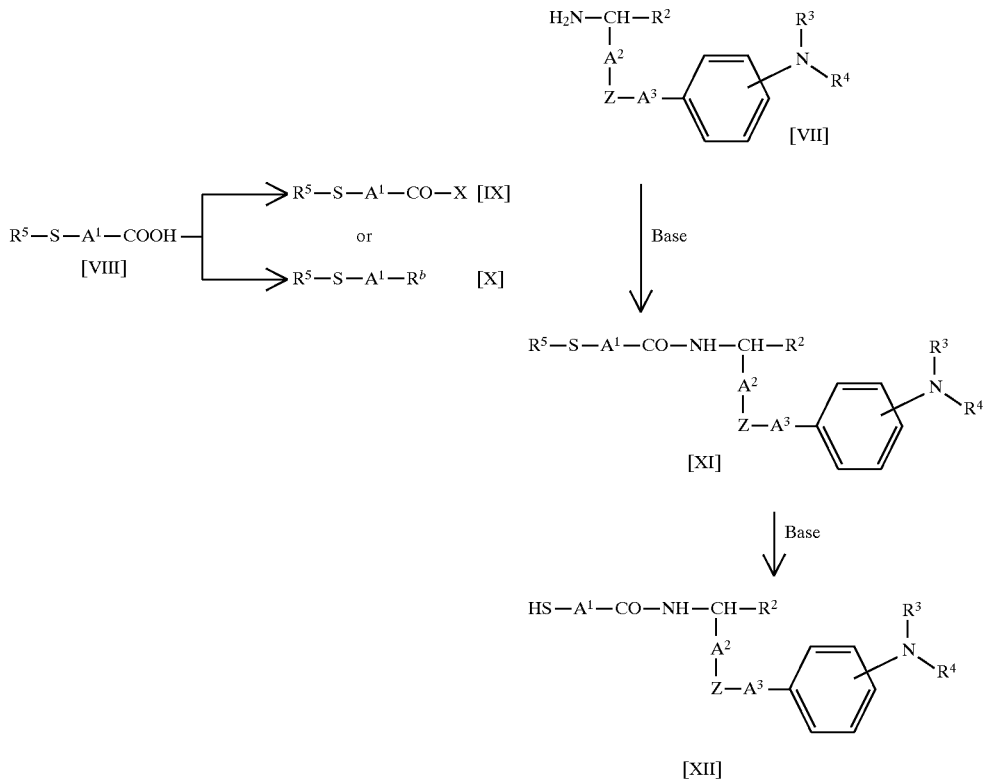

wherein R⁵ represents a lower alkanoyl group or a benzoyl group, the phenyl ring in the benzoyl group can be substituted by a halogen atom, a lower alkyl group or a lower alkoxy group.

$R^a$ represents an amino protecting group for amino acid.
$R^b$ represents an active ester of carboxylic acid.
X represents a halogen atom.

The above newly defined groups will be described in detail. The amino protecting group for amino acid indicates those which are widely used as a group for protecting an amino group of amino acid, such as an urethane type protecting group such as a tert-butoxycarbonyl group or a benzyloxycarbonyl group; an acyl type protecting group such as a formyl group; or an alkyl type protecting group such as a trityl group. The active ester indicates those which are widely used as an active ester of amino acid, such as a 4-nitrophenylester or an N-hydroxysuccinimidoester.

The compound represented by the above formula [III] is reacted with the compound represented by the formula [V] which is derived from the compound represented by the formula [IV] in the presence of a base to obtain the compound represented by the formula [VI], from which the amino protecting group $R^a$ is subsequently removed from the compound [VI] to obtain the compound represented by the formula [VII]. Then, the compound represented by the formula [VIII] is converted into an acid halide represented by the formula [IX] or an active ester compound represented by the formula [X], and the compound [IX] or [X] is reacted with the above compound [VII] in the presence of a base to obtain the present compound (formula [XI]) wherein $R^1$ is a lower alkanoyl group or a benzoyl group (a phenyl ring thereof can be substituted by a halogen atom, a lower alkyl group or a lower alkoxy group). Then, the lower alkanoyl group, or the benzoyl group in which the phenyl ring can be substituted by the halogen atom, the lower alkyl group or the lower alkoxy group is removed from the compound [XI] in the presence of a base to obtain the present compound (formula [XII]) wherein $R^1$ is hydrogen.

Additionally, a carboxyl group in the present compound can be converted into an ester using a conventional method, if necessary. Conversely, an ester can be hydrolyzed into a carboxylic acid using a conventional method.

The compounds obtained in the above process can be converted into salts as described above according to a conventional method.

A diastereoisomer and an optical isomer are present in the compound represented by the formula [I], which are all included in the present invention. When an optically active raw material is used, a single diastereoisomer or an optical isomer is obtained. When a racemic compound is used as a raw material, various isomers can be separated by a conventional method, for example, a method using an optical resolving agent or the like.

In order to investigate the utility of the present compound, the activity of the present compound on $LTA_4$ hydrolase was studied. Study was done using as an index an amount of $LTB_4$ produced by an enzymatic reaction using $LTA_4$ as a substrate and, as a result, the present compound exhibited strong inhibitory activity on $LTA_4$ hydrolase (details will be described in the item of pharmacological experiment below). From this, the present compound is useful for a various diseases where $LTB_4$, which is produced by an enzymatic reaction, is concerned.

The present compound can be administered orally or parenterally. Examples of dosage form are tablets, capsules, granules, powders, injections and the like. The present compound may be formulated into preparations using a conventional technique. For example, in a case of oral preparations such as tablets, capsules, granules and powders, a bulking agent such as lactose, crystalline cellulose, starch or vegetable oil, a lubricant such as magnesium stearate or talc, a binding agent such as hydroxypropylcellulose or polyvinylpyrrolidone, a disintegrating agent such as calcium carboxymethylcellulose or low-substituted hydroxypropylmethylcellulose, a coating agent such as hydroxypropylmethylcellulose, macrogol or silicone resin, and a film forming agent such as gelatin film can be added, if necessary.

A dose of the present compound can be appropriately selected depending upon symptoms, age, dosage form and the like. In the case of oral preparations, a dose of 0.1 to 5000 mg, preferably 1 to 1000 mg per day can be administered once or a few times.

PREFERRED EMBODIMENTS FOR CARRYING OUT THE INVENTION

Preparations, formulations and results of pharmacological experiments of the present compounds are shown below, and they are intended for better understanding the present invention but are not to limit the scope of the present invention.

PREPARATION

Reference Example 1

(2R)-2-tert-Butoxycarbonylamino-3-[4-(N,N-dimethylamino)benzylthio]propionic acid (Reference compound No. 1-1)

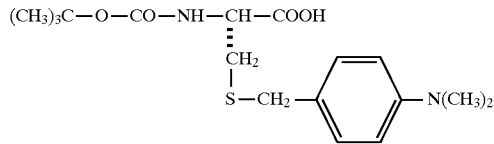

4-(N,N-Dimethylamino)benzylalcohol (2.0 g) is dissolved in 47% hydrobromic acid (13.5 ml), and the solution is stirred at 120°–130° C. for two hours and 30 minutes in a sealed tube. The reaction solution is concentrated under reduced pressure to obtain an oil. Then, a 5% aqueous citric acid solution (30 ml) is added to N-tert-butoxycarbonyl-L-cysteinedicyclohexylamine salt (2.42 g), and the whole is extracted with methylene chloride (30 ml). The organic layer is washed with a saturated sodium chloride solution and dried over anhydrous sodium sulfate to obtain a solution of N-tert-butoxycarbonyl-L-cysteine in methylene chloride. To this solution is added N,N-diisopropylethylamine (4.7 ml) under ice-cooling, the mixture is added to the previously obtained oil while stirring, and stirring is continued at room temperature for two hours and 30 minutes. The reaction solution is concentrated under reduced pressure to distill methylene chloride off, a 5% aqueous citric acid solution is added thereto, and the whole is extracted with ethyl acetate. The organic layer is washed with a 5% aqueous citric acid solution then a saturated solution of sodium chloride, dried over anhydrous sodium sulfate and concentrated under reduced pressure. The resulting oil is purified by silica gel column chromatography to obtain 1.32 g (62.0%) of the titled compound.

Optical isomer of Reference compound No. 1-9

$[\alpha]_D^{20}$ −29.8° (c=1.0, methanol); IR (Film, cm$^{-1}$) 3415, 2978, 1711, 1613, 1520, 1246, 1166, 1050

The following compounds are obtained by a method similar to Reference Example 1.

(2R)-2-tert-Butoxycarbonylamino-3-[4-(N-ethyl-N-methylamino)benzylthio]propionic acid (Reference compound No. 1-2)

(2R)-2-tert-Butoxycarbonylamino-3-[4-(N-isopropyl-N-methylamino)benzylthio]propionic acid (Reference compound No. 1-3)

(2R)-2-tert-Butoxycarbonylamino-3-[4-(N-tert-butyl-N-methylamino)benzylthio]propionic acid (Reference compound No. 1-4)

(2R)-2-tert-Butoxycarbonylamino-3-[4-(N,N-diethylamino)benzylthio]propionic acid (Reference compound No. 1-5)

$[\alpha]_D^{20}$ −26.6° (c=0.47, methanol); IR (Film, cm$^{-1}$) 3428, 2976, 1710, 1612, 1519, 1368, 1167, 1056, 755

(2S)-2-tert-Butoxycarbonylamino-4-[4-(N,N-dimethylamino)benzylthio]butyric acid (Reference compound No. 1-6)

$[\alpha]_D^{20}$ −9.5° (c=0.34, methanol); IR (Film, cm$^{-1}$) 3325, 2976, 2930, 1709, 1520, 1227, 1165, 1050

(2S)-2-tert-Butoxycarbonylamino-6-[4-(N,N-dimethylamino)benzylthio]hexanoic acid (Reference compound No. 1-7)

(2R)-2-tert-Butoxycarbonylamino-3-[3-(N,N-dimthylamino)benzylthlo]propionic acid (Reference compound No. 1-8)

$[\alpha]_D^{20}$ −38.5° (c=0.48, methanol); IR (Film, cm$^{-1}$) 3332, 1709, 1580, 1392, 1337, 1246

(2S)-2-tert-Butoxycarbonylamino-3-[4-(N,N-dimethylamino)benzylthio]propionic acid (Reference compound No. 1-9)

Optical isomer of Reference compound No. 1-1

$[\alpha]_D^{20}$ +34.1° (c=1.0, methanol); IR (Film, cm$^{-1}$) 3322, 2977, 2930, 1713, 1613, 1520, 1392, 1246, 1165, 1056

Reference Example 2

(2S)-2-tert-Butoxycarbonylamino-3-[4-(N,N-dimethylamino)benzyloxy]propionic acid (Reference compound No. 2-1)

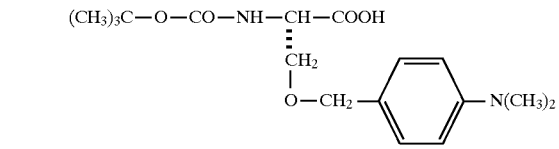

4-(N,N-Dimethylamino)benzylalcohol (1.62 g) is dissolved in 47% hydrobromic acid (11.1 ml), and the solution is stirred at 120°–130° C. for one hour and 30 minutes in a sealed tube. The reaction solution is concentrated under reduced pressure to obtain an oil. Then, a solution of N-tert-butoxycarbonyl-L-serine (2 g) in dimethylformamide (10 ml) is added dropwise to a suspension of 60% sodium hydride in dimethylformamide (10 ml) under ice-cooling, and the mixture is further stirred for 40 minutes. After the mixture is added to the previously obtained oil while stirring, the mixture is stirred at room temperature for one hour and 30 minutes. To the reaction solution is added N,N-diisopropylethylamine (1.68 ml), followed by further stirring at room temperature for two days. The reaction solution is concentrated under reduced pressure, and an aqueous saturated sodium hydrogencarbonate solution is added thereto. The mixture is washed with diethyl ether. The aqueous layer is acidified by the addition of a 10% aqueous citric acid solution and extracted with diethyl ether. The organic layer is washed with a saturated sodium chloride solution, dried over anhydrous magnesium sulfate and concentrated under reduced pressure. The resulting oil is purified by silica gel column chromatography to obtain 240 mg (7.3%) of the titled compound.

Optical isomer of Reference compound No. 2-7

IR (Film, cm$^{-1}$) 3648, 3433, 1708, 1520, 1165, 1059

The following compounds are obtained by a method similar to Reference Example 2.

(2S)-2-tert-Butoxycarbonylamino-3-[4-(N-ethyl-N-methylamino)benzyloxy]propionic acid (Reference compound No. 2-2)

(2S)-2-tert-Butoxycarbonylamino-3-[4-(N,N-diethylamino)benzyloxy]propionic acid (Reference compound No. 2-3)

(2S)-2-tert-Butoxycarbonylamino-4-[4-(N,N-dimethylamino)benzyloxy]butyric acid (Reference compound No. 2-4)

(2S)-2-tert-Butoxycarbonylamino-6-[4-(N,N-dimethylamino)benzyloxy]hexanoic acid (Reference compound No. 2-5)

(2S)-2-tert-Butoxycarbonylamino-3-[3-(N,N-dimethylamino)benzyloxy]propionic acid (Reference compound No. 2-6)

(2R)-2-tert-Butoxycarbonylamino-3-[4-(N,N-dimethylamino)benzyloxy]propionic acid (Reference compound No. 2-7)

Optical isomer of Reference compound No. 2-1

Reference Example 3

(2R)-2-Amino-3-[4-(N,N-dimethylamino)benzylthio]propionic acid dihydrochloride (Reference compound No. 3-1)

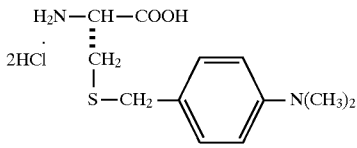

Under ice-cooling, anisole (613 μl) and 4N hydrochloric acid/dioxane (10 ml) are added to (2R)-2-tert-butoxycarbonylamino-3-[4-(N,N-dimethylamino)benzylthio]propionic acid (Reference compound No. 1-1, 1.0 g), and the mixture is stirred at room temperature for one hour. The reaction solution is concentrated under reduced pressure, and the resulting oil is washed with diethyl ether to obtain 0.84 g (91.0%) of the titled compound.

Optical isomer of Reference compound No. 3-14

$[\alpha]_D^{20}$ −19.6° (c=1.0, methanol); IR (Film, cm$^{-1}$) 3397, 2906, 1966, 1741, 1606

The following compounds are obtained by a method similar to Reference Example 3.

(2R)-2-Amino-3-[4-(N-ethyl-N-methylamino)benzylthio]propionic acid dihydrochloride (Reference compound No. 3-2)

(2R)-2-Amino-3-[4-(N-isopropyl-N-methylamino)benzylthio]propionic acid dihydrochloride (Reference compound No. 3-3)

(2R)-2-Amino-3-[4-(N-tert-butyl-N-methylamino)benzylthio]propionic acid dihydrochloride (Reference compound No. 3-4)

(2R)-2-Amino-3-[4-(N,N-diethylamino)benzylthio]propionic acid dihydrochloride (Reference compound No. 3-5)

(2S)-2-Amino-4-[4-(N,N-dimethylamino)benzylthio]butyric acid dihydrochloride (Reference compound No. 3-6)

$[\alpha]_D^{20}$ +13.6° (c=0.53, methanol); IR (KBr, cm$^{-1}$) 2920, 2023, 1735, 1604, 1510, 1204, 1131

(2S)-2-Amino-6-[4-(N,N-dimethylamino)benzylthio]hexanoic acid dihydrochloride (Reference compound No. 3-7)

(2S)-2-Amino-3-[4-(N,N-dimethylamino)benzyloxy]propionic acid dihydrochloride (Reference compound No. 3-8)

Optical isomer of Reference compound No. 3-16

(2S)-2-Amino-3-[4-(N-ethyl-N-methylamino)benzyloxy]propionic acid dihydrochloride (Reference compound No. 3-9)

(2S)-2-Amino-3-[4-(N,N-diethylamino)benzyloxy]propionic acid dihydrochloride (Reference compound No. 3-10)

(2S)-2-Amino-4-[4-(N,N-dimethylamino)benzyloxy]butyric acid dihydrochloride (Reference compound No. 3-11)

(2S)-2-Amino-6-[4-(N,N-dimethylamino)benzyloxy]hexanoic acid dihydrochloride (Reference compound No. 3-12)

(2R)-2-Amino-3-[3-(N,N-dimethylamino)benzylthio]propionic acid dihydrochloride (Reference compound No. 3-13)

$[\alpha]_D^{20}$ −32.1° (c=0.52, methanol); IR (KBr, cm$^{-1}$) 3408, 2858, 1743, 1595, 1502

(2S)-2-Amino-3-[4-(N,N-dimethylamino)benzylthio]propionic acid (Reference compound No. 3-14)

$[\alpha]_D^{20}$ +18.3° (c=1.0, methanol); IR (Film, cm$^{-1}$) 3410, 2917, 2003, 1739, 1616, 1324

Optical isomer of Reference compound No. 3-1

(2R)-2-Amino-3-[3-(N,N-dimethylamino)benzyloxy]propionic acid (Reference compound No. 3-15)

2S)-2-Amino-3-[4-(N,N-dimethylamino)benzyloxy]propionic acid (Reference compound No. 3-16)

Optical isomer of Reference compound No. 3-8

Reference Example 4

(2S)-3-Benzoylthio-2-methylpropionyl chloride (Reference compound No. 4-1)

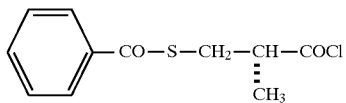

Thionyl chloride (5.69 ml) is added to (2S)-3-benzoylthio-2-methylpropionic acid (13.5 g) under ice-cooling, and the mixture is stirred at room temperature overnight. The reaction solution is concentrated under reduced pressure to obtain 15 g (quantitative) of the titled compound.

IR (Film, cm$^{-1}$) 1786, 1668, 1448, 1209, 1177

Reference Example 5

4-Nitrophenyl (2S)-3-benzoylthio-2-methylpropionate Reference compound No. 5-1)

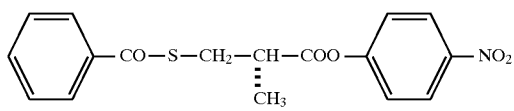

To a solution of (2S)-3-benzoylthio-2-methylpropionic acid (15 g) in methylene chloride (100 ml) are successively added 4-nitrophenol (10.2 g) and dicyclohexylcarbodiimide (15.2 g) under ice-cooling, and the mixture is stirred under ice-cooling for 30 minutes and at room temperature for four hours and 30 minutes. The resulting precipitates are filtered out, and the filtrate is concentrated under reduced pressure. The resulting oil is purified by silica gel column chromatography to obtain 26.01 g (quantitative) of the titled compound.

An optical isomer of Reference compound No. 5-8 mp 42.0°–44.0° C.

$[\alpha]_D^{20}$ –101.2° (c=1.0, methanol); IR (KBr, cm$^{-1}$) 3079, 2988, 1759, 1660, 1592, 1521, 1351, 1323, 1204

The following compounds are obtained by a method similar to Reference Example 5.

4-Nitrophenyl benzoylthioacetate (Reference compound No. 5-2)

mp 87.0°–88.2° C.; IR (KBr, cm$^{-1}$) 3082, 2929, 1769, 1659, 1523, 1346, 1210, 1129, 918, 687

4-Nitrophenyl 3-benzoylthiopropionate (Reference compound No. 5-3)

mp 79.2°–80.5° C.; IR (KBr, cm$^{-1}$) 3114, 3089, 1765, 1665, 1523, 1347, 1204, 1124, 908, 689

4-Nitrophenyl 6-benzoylthiohexanate (Reference compound No. 5-4)

4-Nitrophenyl 3-benzoylthio-2,2-dimethylpropionate (Reference compound No. 5-5)

4-Nitrophenyl (2S)-2-benzoylthiopropionate (Reference compound No. 5-6)

Optical isomer of Reference compound No. 5-7

$[\alpha]_D^{20}$ –78.3° (c=1.1, chloroform); IR (Film, cm$^{-1}$) 3084, 2858, 1767, 1523, 1348

4-Nitrophenyl (2R)-2-benzoylthiopropionate (Reference compound No. 5-7)

Optical isomer of Reference compound No. 5-6

$[\alpha]_D^{20}$ +43.9° (c=1.1, chloroform); IR (Film, cm$^{-1}$) 3084, 2857, 1765, 1711, 1524, 1347

4-Nitrophenyl (2RS)-3-benzoylthio-2-methylpropionate (Reference compound No. 5-8)

mp 40.5°–42.0° C.; IR (KBr, cm$^{-1}$) 3076, 2979, 1758, 1661, 1593, 1522, 1346, 1209

4-Nitrophenyl (2RS)-3-benzoylthio-2-ethylpropionate (Reference compound No. 5-9)

IR (Film, cm$^{-1}$) 2967, 2935, 2116, 1761, 1664, 1523, 1347, 1209, 1103, 913, 688

4-Nitrophenyl (2RS)-3-benzoylthio-2-propylpropionate (Reference compound No. 5-10)

IR (Film, cm$^{-1}$) 3084, 1761, 1666, 1616, 1524, 1347

4-Nitrophenyl (2RS)-3-benzoylthio-2-isopropylpropionate (Reference compound No. 5-11)

IR (Film, cm$^{-1}$) 3083, 1758, 1665, 1616, 1524, 1347, 1315

4-Nitrophenyl (2RS)-3-benzoylthio-2-benzylpropionate (Reference compound No. 5-12)

IR (Film, cm$^{-1}$) 2930, 2117, 1761, 1666, 1593, 1524, 1490, 1347, 1207, 1124, 911, 689

4-Nitrophenyl (2RS)-3-benzoylthio-2-phenethylpropionate (Reference compound No. 5-13)

mp 93.8°–96.0° C.; IR (KBr, cm$^{-1}$) 3023, 2932, 1755, 1661, 1522, 1490, 1347, 1205, 1188, 914, 687

4-Nitrophenyl (3RS)-3-benzoylthiobutyrate (Reference compound No. 5-14)

mp 90.5°–93.2° C.; IR (KBr, cm$^{-1}$) 3077, 1763, 1658, 1520, 1461, 1382

4-Nitrophenyl 4-benzoylthiobutyrate (Reference compound No. 5-15)

mp 104.0°–106.5° C.; IR (KBr, cm$^{-1}$) 3327, 2934, 1766, 1645, 1521, 1358, 1219, 1122, 928, 694

4-Nitrophenyl (2RS)-4-benzoylthio-2-methylbutyrate (Reference compound No. 5-16)

IR (Film, cm$^{-1}$) 2936, 1760, 1661, 1524, 1347, 1208, 1129, 912, 689

Reference Example 6

(2R)-2-tert-Butoxycarbonylamino-3-[4-(N,N-dimethylamino)benzylthio]propionic acid methyl amide (Reference compound No. 6-1)

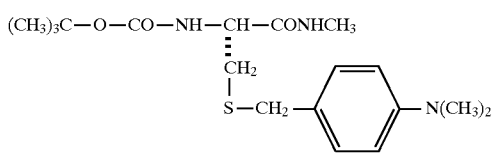

A solution of N-methylmorpholine (0.217 ml) and isobutyl chloroformate (0.256 ml) in tetrahydrofuran (5 ml) is added to a solution of (2R)-2-tert-butoxycarbonylamino-3-[4-(N,N-dimethylamino)benzylthio]propionic acid (Reference compound No. 1-1, 700 mg) in tetrahydrofuran (15 ml) under nitrogen atmosphere and under cryogen (ice-sodium chloride)-cooling, and the mixture is stirred for 15 minutes. Then, a 40% aqueous N-methylamine solution (0.756 ml) is added thereto under cryogen (ice-sodium chloride)-cooling, and the mixture is further stirred for two hours. To the reaction solution is added a 5% aqueous sodium hydrogencarbonate solution, and the mixture is extracted with ethyl acetate. The organic layer is washed with a saturated sodium chloride solution, dried over anhydrous magnesium sulfate and concentrated under reduced pressure. The resulting oil is purified by silica gel column chromatography to obtain 213 mg (29.4%) of the titled compound.

mp 96.0°–104.0° C.; $[\alpha]_D^{20}$ –10.3° (cm=0.47, methanol); IR (KBr, cm$^{-1}$) 3340, 3078, 1685, 1552, 1391, 1365, 1242

The following compound is obtained by a method similar to Reference Example 6.

(2R)-2-tert-Butoxycarbonylamino-3-[4-(N,N-dimethylamino) benzylthio]propionic acid benzyl amide (Reference compound No. 6-2)

EXAMPLE 1

(2R)-2-[(2S)-3-Benzoylthio-2-methylpropionylamino]-3-[4-(N,N-dimethylamino)benzylthio]propionic acid (Compound No. 1-1) and (2S)-2-[(2S)-3-benzoylthio-2-methylpropionylamino]-3-[4-(N,N-dimethylamino) benzylthio]propionic acid (Compound No. 1-2)

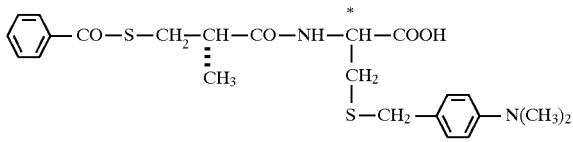

(2S)-3-Benzoylthio-2-methylpropionyl chloride (Reference compound No. 4-1, 888 mg) is added to a solution of (2R)-2-amino-3-[4-(N,N-dimethylamino) benzylthio]propionic acid dihydrochloride (Reference compound No. 3-1, 800 mg) in a mixed solution of 1N aqueous sodium hydroxide solution (9.76 ml)-water (16 ml) under ice-cooling, and the mixture is stirred under ice-cooling for one hour and further at room temperature for two hours and 30 minutes. The reaction solution is acidified by the addition of acetic acid and extracted with ethyl acetate. The organic layer is washed with a 5% aqueous citric acid solution then with a saturated sodium chloride solution, dried over anhydrous sodium sulfate and concentrated under reduced pressure. The resulting oil is purified by silica gel column chromatography to obtain 147.7 mg (Compound No. 1-1, 13.2%) and 184.2 mg (Compound No. 1-2, 16.4%), respectively.

(2R)-2-[(2S)-3-Benzoylthio-2-methylpropionylamino]-3-[4-(N,N-dimethylamino)benzylthio]propionic acid (Compound No. 1-1)

Diastereoisomer of Compound No. 1-2 and Compound No. 2-33 mp 118.0°–119.4° C.; $[\alpha]_D^{20}$ –134.8° (c=0.53, methanol); IR (KBr, cm$^{-1}$) 3343, 2957, 2936, 2466, 1725, 1675, 1642, 1515, 1310, 1213, 1199, 1000

(2S)-2-[(2S)-3-Benzoylthio-2-methylpropionylamino-]3-[4-(N,N-dimethylamino)benzylthio]propionic acid (Compound No. 1-2)

Diastercoisomer of Compound No. 1-1 and enantiomer of Compound No. 2-33 mp 93.5°–97.5° C.; $[-]_D^{20}$ –12.5° (c=1.0, methanol); IR (KBr, cm$^{-1}$) 3351, 2977, 2933, 1712, 1658, 1515, 1203

EXAMPLE 2

(2R)-2-[(2S)-3-Benzoylthio-2-methylpropionylamino]-3-[4-(N,N-dimethylamino)benzylthio]propionic acid (Compound No. 2-1, identical with Compound No. 1-1)

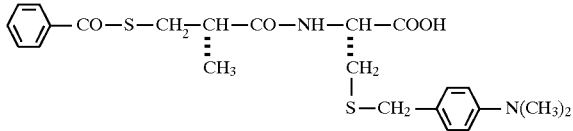

Triethylamine (15.3 ml) is added to a solution of (2R)-2-amino-3-[4-(N,N-dimethylamino)benzylthio]propionic acid dihydrochloride ((Reference compound No. 3-1, 18 g) in a mixed solvent of methylene chloride (500 ml) and N,N-dimethylformamide (100 ml) under ice-cooling and the mixture is stirred. To the reaction mixture is added a solution of 4-nitrophenyl (2S)-3-benzoylthio- 2-methylpropionate ((Reference compound No. 5-1, 18.2 g) in methylene chloride (100 ml) and the mixture is stirred. Triethylamine is added to the reaction mixture to adjust the mixture to pH 9 and stirring is further continued at room temperature for five days. The reaction mixture is adjusted to pH 3 by adding acetic acid and the whole is extracted with ethyl acetate. The organic layer is washed with a 5% aqueous citric acid solution, water and a saturated sodium chloride solution successively, dried over anhydrous sodium sulfate and concentrated under reduced pressure. The obtained oily residue is purified by silica gel column chromatography to give 9.28 g (36.7%) of the titled compound. Physical properties of the obtained compound are identical with those of the compound No. 1-1 obtained in Example 1.

The following compounds are obtained by a method similar to Example 2.

(2R)-2-Benzoylthioacetylamino-3-[4-(N,N-dimethylamino)benzylthio]propionic acid (Compound No. 2-2)

$[\alpha]_D^{20}$ –37.8° (c=0.53, methanol); IR (Film, cm$^{-1}$) 2919, 1730, 1666, 1521, 1209, 914, 754, 689

(2R)-2-(3-Benzoylthiopropionylamino)-3-[4-(N,N-dimethylamino)benzylthio]propionic acid (Compound No. 2-3)

mp 98.0°–103.0° C.; $[\alpha]_D^{20}$ –66.1° (c=0.49, methanol); IR (KBr, cm$^{-1}$) 3344, 1662, 1517, 1403, 1204, 914, 686

(2R)-2-(6-Benzoylthiohexanoylamino)-3-[4-(N,N-dimethylamino)benzylthio]propionic acid (Compound No. 2-4)

(2R)-2-[(2S)-3-Benzoylthio-2-methylpropionylamino]-3-[4-(N-ethyl-N-methylamino)benzylthio]propionic acid (Compound No. 2-5)

(2R)-2-[(2S)-3-Benzoylthio-2-methylpropionylamino]-3-[4-(N-isopropyl-N-methylamino)benzylthio]propionic acid (Compound No. 2-6)

(2R)-2-[(2S)-3-Benzoylthio-2-methylpropionylamino]-3-[4-(N-tert-butyl-N-methylamino)benzylthio]propionic acid (Compound No. 2-7)

(2R)-2-[(2S)-3-Benzoylthio-2-methylpropionylamino]-3-[4-(N,N-diethylamino)benzylthio]propionic acid (Compound No. 2-8)

$[\alpha]_D^{20}$ –122.0° (c=0.45, methanol); IR (Film, cm$^{-1}$) 3306, 2973, 1661, 1612, 1519, 1208, 914, 755, 690

(2S)-2-[(2S)-3-Benzoylthio-2-methylpropionylamino]-4-[4-(N,N-dimethylamino)benzylthio]butyric acid (Compound No. 2-9)

$[\alpha]_D^{20}$ –81.6° (c=0.51, methanol); IR (Film, cm$^{-1}$) 3306, 2931, 1733, 1662, 1521, 1447, 1350, 1208

(2S)-2-[(2S)-3-Benzoylthio-2-methylpropionylamino-]6-[4-(N,N-dimethylamino)benzylthio]hexanoic acid (Compound No. 2-10)

(2R)-2-(3-Benzoylthio-2,2-dimethylpropionylamino)-3-[4-(N,N-dimethylamino)benzylthio]propionic acid (Compound No. 2-11)

(2R)-2-(3-Benzoylthio-2,2-dimethylpropionylamino)-3-[4-(N-ethyl-N-methylamino)benzylthio]propionic acid (Compound No. 2-12)

(2R)-2-(3-Benzoylthio-2,2-dimethylpropionylamino)-3-[4-(N-isopropyl-N-methylamino)benzylthio]propionic acid (Compound No. 2-13)

(2R)-2-(3-Benzoylthio-2,2-dimethylpropionylamino)-3-[4-(N-tert-butyl-N-methylamino)benzylthio]propionic acid (Compound No. 2-14)

(2R)-2-(3-Benzoylthio-2,2-dimethylpropionylamino)-3-[4-(N,N-diethylamino)benzylthio]propionic acid (Compound No. 2-15)

(2S)-2-(3-Benzoylthio-2,2-dimethylpropionylamino)-4-[4-(N,N-dimethylamino)benzylthio]butyric acid (Compound No. 2-16)

(2S)-2-(3-Benzoylthio-2,2-dimethylpropionylamino)-6-[4-(N,N-dimethylamino)benzylthio]hexanoic acid (Compound No. 2-17)

(2S)-2-Benzoylthioacetylamino)-3-[4-(N,N-dimethylamino)benzyloxy]propionic acid (Compound No. 2-18)

(2S)-2-(3-Benzoylthiopropionylamino)-3-[4-(N,N-dimethylamino)benzyloxy]propionic acid (Compound No. 2-19)

(2S)-2-(6-Benzoylthiohexanoylamino)-3-[4-(N,N-dimethylamino)benzyloxy]propionic acid (Compound No. 2-20)

(2S)-2-[(2S)-3-Benzoylthio-2-methylpropionylamino]-3-[4-(N,N-dimethylamino)benzyloxy]propionic acid (Compound No. 2-21)

Diastereo isomer of compound No. 2-46

$[\alpha]_D^{20}$ −34.4° (c=0.39, methanol); IR (Film, cm$^{-1}$) 3305, 2339, 1732, 1661, 1208, 1100

(2S)-2-[(2S)-3-Benzoylthio-2-methylpropionylamino]-3-[4-(N-ethyl-N-methylamino)benzyloxy]propionic acid (Compound No. 2-22)

(2S)-2-[(2S)-3-Benzoylthio-2-methylpropionylamino]-3-[4-(N,N-diethylamino)benzyloxy]propionic acid (Compound No. 2-23)

(2S)-2-[(2S)-3-Benzoylthio-2-methylpropionylamino]-4-[4-(N,N-dimethylamino)benzyloxy]butyric acid (Compound No. 2-24)

(2S)-2-[(2S)-3-Benzoylthio-2-methylpropionylamino]-6-[4-(N,N-dimethylamino)benzyloxy]hexanoic acid (Compound No. 2-25)

(2S)-2-(3-Benzoylthio-2,2-dimethylpropionylamino)-3-[4-(N,N-dimethylamino)benzyloxy]propionic acid (Compound No. 2-26)

(2S)-2-(3-Benzoylthio-2,2-dimethylpropionylamino)-3-[4-(N-ethyl-N-methylamino)benzyloxy]propionic acid (Compound No. 2-27)

(2S)-2-(3-Benzoylthio-2,2-dimethylpropionylamino)-3-[4-(N,N-diethylamino)benzyloxy]propionic acid (Compound No. 2-28)

(2S)-2-(3-Benzoylthio-2,2-dimethylpropionylamino)-4-[4-(N,N-dimethylamino)benzyloxy]butyric acid (Compound No. 2-29)

(2S)-2-(3-Benzoylthio-2,2-dimethylpropionylamino)-6-[4-(N,N-dimethylamino)benzyloxy]hexanoic acid (Compound No. 2-30)

(2R)-2-[(2S)-2-Benzoylthiopropionylamino]-3-[4-(N,N-dimethylamino)benzylthio]propionic acid (Compound No. 2-31)

Diastereo isomer of compound No. 2-32

$[\alpha]_D^{20}$ −97.9° (c=0.19, methanol); IR (Film, cm$^{-1}$) 3367, 2930, 1730, 1662, 1581, 1447

(2R)-2[(2R)-2-Benzoylthiopropionylamino]-3-4-(N,N-dimethylamino)benzylthio]propionic acid (Compound No. 2-32)

Diastereo isomer of compound No. 2-31

$[\alpha]_D^{20}$ +6.5° (c=1.0, methanol); IR (Film, cm$^{-1}$) 3338, 2929, 1731, 1661, 1581, 1447

(2R)-2-[(2R)-3-Benzoylthio-2-methylpropionylamino]-3-[4-(N,N-dimethylamino)benzylthio]propionic acid (Compound No. 2-33)

Diastereo isomer of compound No. 1-1 and enantiomer of compound No. 1-2 mp 93.5°–95.5° C.;

$[\alpha]_D^{20}$ +8.7° (c=0.49, methanol); IR (KBr, cm$^{-1}$) 3351, 2978, 2933, 1710, 1658, 1515, 1203

(2R)-2-[(2RS)-3-Benzoylthio-2-ethylpropionylamino]-3-[4-(N,N-dimethylamino)benzylthio]propionic acid (Compound No. 2-34)

IR (Film, cm$^{-1}$) 3307, 2964, 2932, 1732, 1661, 1612, 1581, 1208, 914, 755, 690

(2R)-2-[(2RS)-3-Benzoylthio-2-propylpropionylamino]-3-[4-(N,N-dimethylamino)benzylthio]propionic acid (Compound No. 2-35)

IR (Film, cm$^{-1}$) 3327, 2957, 2930, 1731, 1662, 1613, 1581, 1521, 1350

(2R)-2-[(2RS)-3-Benzoylthio-2-isopropylpropionylamino]-3-[4-(N,N-dimethylamino)benzylthio]propionic acid (Compound No. 2-36)

IR (Film, cm$^{-1}$) 3307, 1731, 1660, 1521, 1350, 1208

(2R)-2-[(2RS)-3-Benzoylthio-2-benzylpropionylamino]-3-[4-(N,N-dimethylamino)benzylthio]propionic acid (Compound No. 2-37)

IR (Film, cm$^{-1}$) 3306, 2921, 1732, 1661, 1521, 1207, 912, 752, 687

(2R)-2-[(2RS)-3-Benzoylthio-2-phenetylpropionylamino]-3-[4-(N,N-dimethylamino)benzylthio]propionic acid (Compound No. 2-38)

IR (Film, cm$^{-1}$) 3306, 2924, 1733, 1661, 1612, 1521, 1448, 1207, 913, 752, 689

(2R)-2-[(3RS)-3-Benzoylthiobutyrylamino]-3-[4-(N,N-dimethylamino)benzylthio]propionic acid (Compound No. 2-39)

IR (Film, cm$^{-1}$) 3305, 2924, 1728, 1660, 1614, 1521, 1447, 1210

(2R)-2-(2S)-3-Benzoylthio-2-methylpropionylamino]-3-[3-(N,N-dimethylamino)benzylthio]propionic acid (Compound No. 2-40)

$[\alpha]_D^{20}$ −10.5° (c=0.49, methanol); IR (Film, cm$^{-1}$) 3306, 2971, 1732, 1661, 1580, 1448

(2R)-2-(4-Benzoylthiobutyrylamino)-3-[4-(N,N-dimethylamino)benzylthio]propionic acid (Compound No. 2-41)

$[\alpha]_D^{20}$ −44.0° (c=0.57, methanol); IR (Film, cm$^{-1}$) 3326, 2924, 1730, 1660, 1612, 1521, 1208, 914, 755, 690

(2R)-2-[(2S or 2R)-4-Benzoylthio-2-methylbutyrylamino]-3-[4-(N,N-dimethylamino)benzylthio]propionic acid (Compound No. 2-42)

Diastereo isomer of compound No. 2-43

$[\alpha]_D^{20}$ −15.0° (c=0.25, methanol); IR (Film, cm$^{-1}$) 3308, 2930, 1732, 1660, 1521, 1209, 913, 755, 690

(2R)-2-[(2R or 2S)-4-Benzoylthio-2-methylbutyrylamino]-3-[4-(N,N-dimethylamino)benzylthio]propionic acid (Compound No. 2-43)

Diastereo isomer of compound No. 2-42

$[\alpha]_D^{20}$ −66.5° (c=0.25, methanol); IR (Film, cm$^{-1}$) 3306, 2931, 1731, 1660, 1521, 1208, 913, 754, 690

(2S)-2-[(2S)-3-Benzoylthio-2-methylpropionylamino]-3-[4-(N,N-dimethylamino)benzylthio]propionic acid (Compound No. 2-44, identical with compound No. 1-2)

(2S)-2-[(2S)-3-Benzoylthio-2-methylpropionylamino]-3-[3-(N,N-dimethylamino)benzyloxy]propionic acid (Compound No. 2-45)

(2R)-2-[(2S)-3-Benzoylthio-2-methylpropionylamino]-3-[4-(N,N-dimethylamino)benzyloxy]propionic acid (Compound No. 2-46)

Diastereo isomer of compound No. 2-21

EXAMPLE 3

(2R)-3-[4-(N,N-Dimethylamino)benzylthio]-2-[(2S)-3-mercapto-2-methylpropionylamino]propionic acid (Compound No. 3-1)

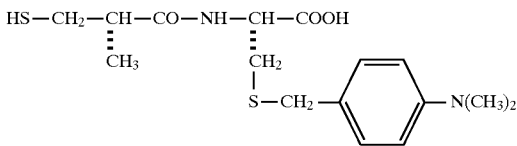

A 28% aqueous ammonia solution (91 ml) is added to (2R)-2-[(2S)-3-benzoylthio-2-methylpropionylamino]-3-[4-(N,N-dimethylamino)benzylthio]propionic acid (Compound No. 1-1, 9.1 g) and the mixture is stirred at room temperature for one hour. The reaction mixture is concentrated under reduced pressure to remove ammonia and the obtained aqueous solution is washed with ethyl acetate. Next the reaction mixture is adjusted to pH 4 by adding acetic acid and the whole is extracted with ethyl acetate. The organic layer is washed with a saturated sodium chloride solution, dried over anhydrous sodium sulfate and concentrated under reduced pressure. The obtained oily residue is purified by silica gel column chromatography to give 5.75 g (81.4%) of the titled compound.

Diastereo isomer of compound Nos. 3-2 and 3-35 mp 104.4°–105.8° C.; $[\alpha]_D^{20}$ –73.7° (c=1.0, methanol); IR (KBr, cm$^{-1}$) 3362,2966, 2929, 2900, 2542, 1707, 1644, 1523, 1217

The following compounds are obtained by a method similar to Example 3.

(2S)-3-[4-(N,N-Dimethylamino)benzylthio]-2-[(2S)-3-mercapto-2-methylpropionylamino]propionic acid (Compound No. 3-2)

Diastereo isomer of compound No. 3-1 and enantiomer of compound No. 3-35 mp 89.5°–91.5° C.; $[\alpha]_D^{20}$ +42.2° (cm=0.47, methanol); IR (KBr, cm$^{-1}$) 3369, 2976, 2930, 2552, 1709, 1651, 1515, 1455, 1347

(2R)-3-[4-(N,N-Dimethylamino)benzylthio]-2-mercaptoacetylaminopropionic acid (Compound No. 3-3)

$[\alpha]_D^{20}$ –35.3° (c=0.55, methanol); IR (Film, cm$^{-1}$) 3305, 2919, 1728, 1651, 1612, 1521, 1349, 1218, 754

(2R)-3-[4-(N,N-Dimethylamino)benzylthio]-2-(3-mercaptopropionylamino)propionic acid (Compound No. 3-4)

$[\alpha]_D^{20}$ –56.5° (c=0.50, methanol); IR (Film, cm$^{-1}$) 3305, 2918, 1728, 1650, 1612, 1521, 1350, 1217, 753

(2R)-3-[4-(N,N-Dimethylamino)benzylthio]-2-(6-mercaptohexanoylamino)propionic acid (Compound No. 3-5)

(2R)-3-[4-(N-Ethyl-N-methylamino)benzylthio]-2-[(2S)-3-mercapto-2-methylpropionylamino]propionic acid (Compound No. 3-6)

(2R)-3-[4-(N-Isopropyl-N-methylamino)benzylthio]-2-[(2S)-3-mercapto-2-methylpropionylamino]propionic acid (Compound No. 3-7)

(2R)-3-[4-(N-tert-Butyl-N-methylamino)benzylthio]-2-[(2S)-3-mercapto-2-methylpropionylamino]propionic acid (Compound No. 3-8)

(2R)-3-[4-(N,N-Diethylamino)benzylthio]-2-[(2S)-3-mercapto-2-methylpropionyl]aminopropionic acid (Compound No. 3-9)

$[\alpha]_D^{20}$ –54.0° (c=0.54, methanol); IR (Film, cm$^{-1}$) 3307, 2972, 1654, 1612, 1519, 1399, 1267, 1196, 1154, 816, 666

(2S)-4-[4-(N,N-Dimethylamino)benzylthio]-2-[(2S)-3-mercapto-2-methylpropionylamino]butyric acid (Compound No. 3-10)

mp 111.5°–115.0° C.; $[\alpha]_D^{20}$ –36.2° (c=0.49, methanol); IR (KBr, cm$^{-1}$) 3302,2973, 2926, 2556, 1728, 1709, 1647, 1525, 1242

(2S)-6-[4-(N,N-Dimethylamino)benzylthio]-2-[(2S)-3-mercapto-2-methylpropionylamino]hexanoic acid (Compound No. 3-11)

(2R)-2-(2,2-Dimethyl-3-mercaptopropionylamino)-3-[4-(N,N-dimethylamino)benzylthio]propionic acid (Compound No. 3-12)

(2R)-3-[4-(N-Ethyl-N-methylamino)benzylthio]-2-(2,2-dimethyl-3-mercaptopropionylamino)propionic acid (Compound No. 3-13)

(2R)-2-(2,2-Dimethyl-3-mercaptopropionylamino)-3-[4-(N-isopropyl-N-methylamino)benzylthio]propionic acid (Compound No. 3-14)

(2R)-3-[4-(N-tert-Butyl-N-methylamino)benzylthio]-2-(2,2-dimethyl-3-mercaptopropionylamino)propionic acid (Compound No. 3-15)

(2R)-3-[4-(N,N-Diethylamino)benzylthio]-2-(2,2-dimethyl-3-mercaptopropionylamino)propionic acid (Compound No. 3-16)

(2S)-2-(2,2-Dimethyl-3-mercaptopropionylamino)-4-[4-(N,N-dimethylamino)benzylthio]butyric acid (Compound No. 3-17)

(2S)-2-(2,2-Dimethyl-3-mercaptopropionylamino)-6-[4-(N,N-dimethylamino)benzylthio]hexanoic acid (Compound No. 3-18)

(2R)-3-[4-(N,N-Dimethylamino)benzylthio]-2-[(2S)-2-mercaptopropionylamino]propionic acid (Compound No. 3-19)

Diastereo isomer of compound No. 3-20

$[\alpha]_D^{20}$ –53.9° (c=0.16, methanol); IR (Film, cm$^{-1}$) 3306, 2926, 2550, 1728, 1659, 1612, 1521

(2R)-3-[4-(N,N-Dimethylamino)benzylthio]-2-[(2R)-2-mercaptopropionylamino]propionic acid (Compound No. 3-20)

Diastereo isomer of compound No. 3-19

$[\alpha]_D^{20}$ –36.5° (c=0.26, methanol); IR (Film, cm$^{-1}$) 3306, 2926, 2552, 1729, 1659, 1612, 1521

(2R)-3-[4-(N,N-Dimethylamino)benzylthio]-2-[(2R)-3-mercapto-2-methylpropionylamino]propionic acid (Compound No. 3-21)

Diastereo isomer of compound No. 3-1 and enantiomer of compound No. 3-2 mp 91.5–92.5° C.; $[\alpha]_D^{20}$ –43.2° (c=0.31, methanol); IR (KBr, cm$^{-1}$) 3368, 2976, 2930, 2557, 1708, 1651, 1515, 1455, 1346

(2R)-3-[4-(N,N-Dimethylamino)benzylthio]-2-[(2RS)-2-ethyl-3-mercaptopropionylamino]propionic acid (Compound No. 3-22)

IR (Film, cm$^{-1}$) 3305, 2963, 2930, 1731, 1656, 1612, 1522, 1350, 1216, 755

(2R)-3-[4-(N,N-Dimethylamino)benzylthio]-2-[(2RS)-3-mercapto-2-propylpropionylamino]propionic acid (Compound No. 3-23)

IR (Film, cm$^{-1}$) 3305, 2957, 2930, 2557, 1729, 1651, 1612, 1521

(2R)-3-[4-(N,N-Dimethylamino)benzylthio]-2-[(2RS)-2-isopropyl-3-mercaptopropionylamino]propionic acid (Compound No. 3-24)

IR (Film, cm⁻¹) 3306, 2555, 1730, 1653, 1521, 1350, 1217

(2R)-2-[(2RS)-2-Benzyl-3-mercaptopropionylamino]-3-[4-(N,N-dimethylamino)benzylthio]propionic acid (Compound No. 3-25)

IR (Film, cm⁻¹) 3305, 2922, 1729, 1651, 1612, 1521, 1350, 1218, 821, 753, 701

(2R)-3-[4-(N,N-Dimethylamino)benzylthio]-2-[(2S or 2R)-2-phenetyl-3-mercaptopropionylamino]propionic acid (Compound No. 3-26)

Diastereo isomer of compound No. 3-27

[α]$_D^{20}$ −34.2° (c=0.87, methanol); IR (Film, cm⁻¹) 3306, 2926, 1731, 1652, 1612, 1521, 1454, 1350, 1217, 753, 700

(2R)-3-[4-(N,N-Dimethylamino)benzylthio]-2-[(2R or 2S)-2-phenetyl-3-mercaptopropionylamino]propionic acid (Compound No. 3-27)

Diastereo isomer of compound No. 3-26

[α]$_D^{20}$ −53.4° (c=0.74, methanol); IR (Film, cm⁻¹) 3306, 2925, 1730, 1651, 1612, 1521, 1454, 1350, 1218, 753, 700

(2R)-3-[4-(N,N-Dimethylamino)benzylthio]-2-[(3RS)-3-mercaptobutyrylamino]propionic acid (Compound No. 3-28)

IR (Film, cm⁻¹) 3306, 2922, 2554, 1651, 1522, 1446, 1351

(2R)-3-[3-(N,N-Dimethylamino)benzylthio]-2-[(2S)-3-mercapto-2-methylpropionylamino]propionic acid (Compound No. 3-29)

[α]$_D^{20}$ −70.8° (c=0.46, methanol); IR (Film, cm⁻¹) 3306, 2972, 2557, 1729, 1658, 1603, 1439, 851

(2R)-3-[4-(N,N-Dimethylamino)benzylthio]-2-(4-mercaptobutyrylamino)propionic acid (Compound No. 3-30)

[α]$_D^{20}$ −45.4° (c=0.48, methanol); IR (Film, cm⁻¹) 3306, 2923, 1723, 1612, 1522, 1414, 1350, 1224, 946, 822

(2R)-3-[4-(N,N-Dimethylamino)benzylthio]-2-[(2S or 2R)-4-mercapto-2-methylbutyrylamino]propionic acid (Compound No. 3-31)

Diastereo isomer of compound No. 3-32

[α]$_D^{20}$ −33.9° (c=0.32, methanol); IR (Film, cm⁻¹) 3305, 2931, 1731, 1650, 1612, 1521, 1349, 1215, 946, 821, 754

(2R)-3-[4-(N,N-Dimethylamino)benzylthio]-2-[(2R or 2S)-4-mercapto-2-methylbutyrylamino]propionic acid (Compound No. 3-32)

Diastereo isomer of compound No. 3-31

[α]$_D^{20}$ −68.1° (c=0.93, methanol); IR (Film, cm⁻¹) 3306, 2932, 1730, 1612, 1521, 1217, 947, 821, 755

EXAMPLE 4

(2RS)-3-[4-(N,N-Dimethylamino)benzyloxy]-2-[(2S)-3-mercapto-2-methylpropionylamino]propionic acid (Compound No. 4-1)

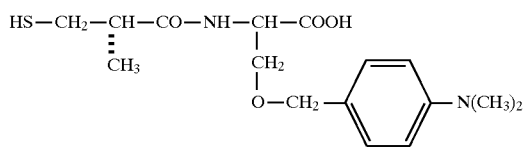

A 28% aqueous ammonia solution (2 ml) is added to (2S)-2-[(2S)-3-benzoylthio-2-methylpropionylamino]-3-[4-(N,N-dimethylamino)benzyloxy]propionic acid (Compound No. 2-33, 85 mg) and the mixture is stirred at room temperature for 20 minutes. The reaction mixture is concentrated under reduced pressure to remove ammonia and the obtained aqueous solution is washed with diethyl ether. Next the reaction mixture is acidified with acetic acid and the whole is extracted with ethyl acetate. The organic layer is washed with a saturated sodium chloride solution, dried over anhydrous magnesium sulfate and concentrated under reduced pressure. The obtained oily residue is purified by silica gel column chromatography to give 11 mg (16.9%) of the titled compound.

IR (Film, cm⁻¹) 3317, 2930, 2360, 1730, 1523, 1102, 811

The following compounds are obtained by a method similar to Example 4.

(2RS)-3-[4-(N,N-Dimethylamino)benzyloxy]-2-mercaptoacetylaminopropionic acid (Compound No. 4-2)

(2RS)-3-[4-(N,N-Dimethylamino)benzyloxy]-2-(3-mercaptopropionylamino)propionic acid (Compound No. 4-3)

(2RS)-3-[4-(N,N-Dimethylamino)benzyloxy]-2-(6-mercaptohexanoylamino)propionic acid (Compound No. 4-4)

(2RS)-3-[4-(N-Ethyl-N-methylamino)benzyloxy]-2-[(2S)-3-mercapto-2-methylpropionylamino]propionic acid (Compound No. 4-5)

(2RS)-3-[4-(N,N-Diethylamino)benzyloxy]-2-[(2S)-3-mercapto-2-methylpropionylamino]propionic acid (Compound No. 4-6)

(2RS)-4-[4-(N,N-Dimethylamino)benzyloxy]-2-[(2S)-3-mercapto-2-methylpropionylamino]butyric acid (Compound No. 4-7)

(2RS)-6-[4-(N,N-Dimethylamino)benzyloxy]-2-[(2S)-3-mercapto-2-methylpropionylamino]hexanoic acid (Compound No. 4-8)

(2RS)-2-(2,2-Dimethyl-3-mercaptopropionylamino)-3-[4-(N,N-dimethylamino)benzyloxy]propionic acid (Compound No. 4-9)

(2RS)-3-[4-(N-Ethyl-N-methylamino)benzyloxy]-2-(2,2-dimethyl-3-mercaptopropionylamino)propionic acid (Compound No. 4-10)

(2RS)-3-[4-(N,N-Diethylamino)benzyloxy]-2-(2,2-dimethyl-3-mercaptopropionylamino)propionic acid (Compound No. 4-11)

(2RS)-2-(2,2-Dimethyl-3-mercaptopropionylamino)-4-[4-(N,N-dimethylamino)benzyloxy]butyric acid (Compound No. 4-12)

(2RS)-2-(2,2-Dimethyl-3-mercaptopropionylamino)-6-[4-(N,N-dimethylamino)benzyloxy]hexanoic acid (Compound No. 4-13)

(2RS)-3-[3-(N,N-Dimethylamino)benzyloxy]-2-[(2S)-3-mercapto-2-methylpropionylamino]propionic acid (Compound No. 4-14)

EXAMPLE 5

(2R)-2-[(2S)-3-Benzoylthio-2-methylpropionylamino]-3-[4-(N,N-dimethylamino)benzylthio]propionic acid methylamide (Compound No. 5-1)

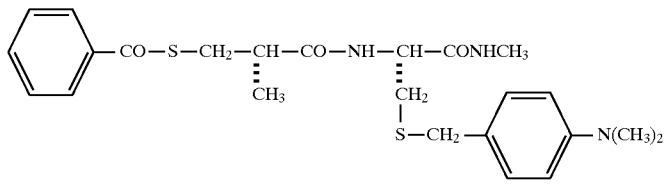

To (2R)-2-tert-butoxycarbonylamino-3-[4-(N,N-dimethylamino)benzylthio]propionic acid methylamide (Reference compound No. 6-1, 200 mg) is added 4N hydrochloric acid/dioxane (1.5 ml) and the mixture is stirred at room temperature for one hour. The reaction mixture is concentrated under reduced pressure and the obtained oily residue is dissolved in methylene chloride (5 ml). To the solution are added N-methylmorphorin (0.119 ml), 1-hydroxybenzotriazoic (109 mg), (2S)-3-benzoylthio-2-methylpropionic acid (182 mg), 1-ethyl-3-(3-dimethylaminopropyl)carbodiimide hydrochloride (135 mg) and N-methylmorphorin (0.077 ml) successively under ice-cooling, and the mixture is stirred at room temperature overnight. To the reaction mixture is added a 5% aqueous sodium hydrogencarbonate solution and the whole is extracted with ethyl acetate, The organic layer is washed with a 5% aqueous sodium hydrogencarbonate solution and a saturated sodium chloride solution successively, dried over anhydrous magnesium sulfate and concentrated under reduced pressure. The obtained oily residue is purified by silica gel column chromatography to give 170 mg (66.4%) of the titled compound.

mp 137.0°–155.0° C.; $[\alpha]_D^{20}$ –99.7° (c=0.49, methanol); IR (KBr, cm$^{-1}$) 3281, 3066, 1640, 1521, 1410

The following compound is obtained by a method similar to Example 5.

(2R)-2-[(2S)-3-Benzoylthio-2-methylpropionylamino]-3-[4-(N,N-dimethylamino)benzylthio]propionic acid benzylamide (Compound No. 5-2)

EXAMPLE 6

(2R)-3-[4-(N,N-Dimethylamino)benzylthio]-2-[(2S)-3-mercapto-2-methylpropionylamino]propionic acid methylamide (Compound No. 6-1)

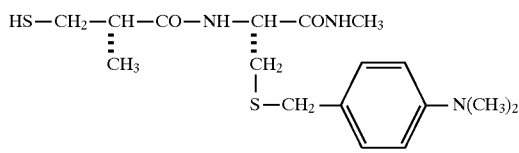

To a solution of (2R)-2-[(2S)-3-benzoylthio-2-methylpropionylamino]-3-[4-(N,N-dimethylamino)benzylthio]propionic acid methylamide (Compound No. 5-1, 50 mg) in methanol (2 ml) is added 1N sodium hydroxide (0.13 ml) and the mixture is stirred at room temperature for 15 minutes. The reaction mixture is adjusted to pH 7 by adding a 5% aqueous citric acid solution and concentrated under reduced pressure. Water is added to the obtained oily residue and the whole is extracted with ethyl acetate. The organic layer is washed with a saturated sodium chloride solution, dried over anhydrous magnesium sulfate and concentrated under reduced pressure to give 18 mg (46.2%) of the titled compound.

mp 133.0°–137.0° C.; $[\alpha]_D^{20}$ –43.8° (c=0.20, chloroform); IR (KBr, cm$^{-1}$) 3292,2556, 1639, 1524, 1355

The following compound is obtained by a method similar to Example 6.

(2R)-3-[4-(N,N-Dimethylamino)benzylthio]-2-[(2S)-3-mercapto-2-methylpropionylamino]propionic acid benzylamide (Compound No. 6-2)

EXAMPLE 7

(2R)-3-[4-(N,N-Dimethylamino)benzylthio]-2-[(2S)-2-methyl-3-methylthioproplonylamino]propionic acid (Compound No. 7-1)

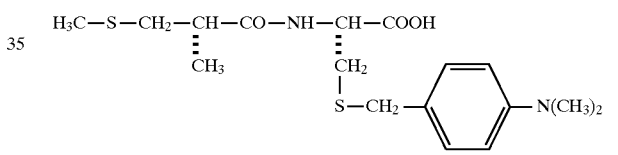

To a solution of (2R)-3-[4-(N,N-dimethylamino)benzylthio]-2-[(2S)-3-mercapto-2-methylpropionylamino]propionic acid (Compound No. 3-1, 300 mg) in ethanol (6.4 ml) is added 2N sodium hydroxide (0.84 ml) under ice-cooling. To the mixture is added a solution of methyl iodide (0.052 ml) in ethanol (2 ml) dropwise and the obtained mixture is stirred for 25 minutes. The reaction mixture is adjusted to pH 4 by adding a 5% aqueous citric acid solution and the whole is extracted with ethyl acetate. The organic layer is washed with a 5% aqueous citric acid solution and a saturated sodium chloride solution successively, dried over anhydrous magnesium sulfate and concentrated under reduced pressure. The obtained oily residue is purified by silica gel column chromatography to give 143 mg (50.3%) of the titled compound.

$[\alpha]_D^{20}$ –76.1° (c=0.31, methanol); IR (Film, cm$^{-1}$) 3306, 2970, 1890, 1731, 1650, 1522, 1424, 1130, 668

The following compound is obtained by a method similar to Example 7.

(2R)-3-[4-(N,N-Dimethylamino)benzylthio]-2-[(2S)-3-benzylthio-2-methylpropionylamino]propionic acid (Compound No. 7-2)

$[\alpha]_D^{20}$ –49.1° (c=0.51, methanol); IR (Film, cm$^{-1}$) 3307, 2917, 1730, 1657, 1612, 1521, 1453, 1351, 1217, 755, 703

EXAMPLE 8

Ethyl (2R)-3-[4-(N,N-dimethylamino)benzylthio]-2-[(2S)-3-mercapto-2-methylpropionylamino]propionate (Compound No. 8-1)

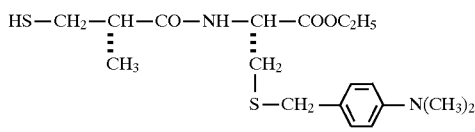

Anhydrous sodium sulfate (3 g) is added to a solution of (2R)-3-[4-(N,N-dimethylamino)benzylthio]-2-[(2S)-3-mercapto-2-methylpropionylamino]propionic acid (Compound No. 3-1, 300 mg) and p-toluenesulfonic acid monohydrate (240 mg) in ethanol (10 ml), and the mixture is refluxed for 3.5 hours. Sodium sulfate is removed by filtration and the filtrate is concentrated under reduced pressure. To the obtained oily residue is added a 5% aqueous sodium hydrogencarbonate solution and the whole is extracted with ethyl acetate. The organic layer is washed with a 5% aqueous sodium hydrogencarbonate solution, a 5% aqueous citric acid solution and a saturated sodium chloride solution successively, dried over anhydrous sodium sulfate and concentrated under reduced pressure to give 211 mg (65.3%) of the titled compound.

mp 60.5°–64.0° C.; $[\alpha]_D^{20}$ –84.5° (c=0.48, methanol); IR (KBr, cm$^{-1}$) 3295, 2974, 2574, 1722, 1648, 1524, 1446, 1058, 811

The following compounds are obtained by a method similar to Example 8.

Benzyl (2R)-3-[4-(N,N-dimethylamino)benzylthio]-2-[(2S)-3-mercapto-2-methylpropionylamino]propionate (Compound No. 8-2)

Ethyl (2R)-2-(2,2-dimethyl-3-mercaptopropionylamino)-3-[4-(N,N-dimethylamino)benzylthio]propionate (Compound No. 8-3)

Benzyl (2R)-2-(2,2-dimethyl-3-mercaptopropionylamino)-3-[4-(N,N-dimethylamino)benzylthio]propionate (Compound No. 8-4) Formulation General formulation examples of oral preparations and injections using the present compounds are shown below.

1) Tablet

Formulation 1 in 100 mg
present compound 1 mg
lactose 66.4 mg
cornstarch 20 mg
calcium carboxymethylcellulose 6 mg
hydroxypropylcellulose 4 mg
magnesium stearate 0.6 mg Tablets according to the prescription as above are coated with 2 mg/tablet of a coating agent (this is a conventional coating agent such as hydroxypropylmethylcellulose, macrogol or silicone resin) to obtain desired coated tablets. (The same is applied to tablets mentioned below.)

Formulation 2 in 100 mg
present compound 5 mg
lactose 62.4 mg
cornstarch 20 mg
calcium carboxymethylcellulose 6 mg
magnesium stearate 0.6 mg
hydroxypropylcellulose 4 mg
coating agent 2 mg Formulation 3 in 100 mg
present compound 20 mg
lactose 51 mg
cornstarch 15 mg
calcium carboxymethylcellulose 5 mg
hydroxypropylcellulose 5 mg
magnesium stearate 1 mg
talc 1 mg
coating agent 2 mg Formulation 4 in 100 mg
present compound 40 mg
lactose 34 mg
cornstarch 10 mg
calcium carboxymethylcellulose 5 mg
hydroxypropylcellulose 5 mg
magnesium stearate 2 mg
talc 2 mg
coating agent 2 mg Formulation 5 in 220 mg
present compound 100 mg
lactose 67 mg
cornstarch 20 mg
calcium carboxymethylcellulose 10 mg
hydroxypropylcellulose 10 mg
magnesium stearate 4 mg
talc 4 mg
coating agent 5 mg 2) Capsule Formulation 1 in 150 mg
present compound 5 mg
lactose 145 mg Varying the mixing ratio of the present compound to lactose, capsules having the contents of the present compound of 10 mg/capsule, 30 mg/capsule, 50 mg/capsule and 100 mg/capsule are also prepared.

3) Granule

Formulation 1 in 100 mg
present compound 30 mg
mannitol 46.5 mg
polyvinyl pyrrolidone K-30 7 mg
eudragit RL 15 mg
triacetin 1.5 mg Formulation 2 in 130 mg
present compound 50 mg
lactose 55 mg
white potato starch 20 mg
hydroxypropylcellulose 4 mg
talc trace 4) Injection Formulation 1 in 10 ml
present compound 10–100 mg
sodium chloride 90 mg
sodium hydroxide q.s.
sterile purified water q.s.

PHARMACOLOGICAL TEST

Izumi et al. had reported a method of measuring $LTA_4$ hydrolase activity by measuring an amount of $LTB_4$ produced by an enzymatic reaction using $LTA_4$ as a substrate (Biochem. Biophys. Res. Commun., 135, 139–145 (1986)). Effects of the present compounds on $LTA_4$ hydrolase were examined according to the method described in the literature.

Experimental Method

An enzyme preparation used in this pharmacological test was prepared by extracting roughly from guinea pig lung by the following method, according to the method of Izumi et al. (Biochem. Biophys. Res. Commun., 135, 139–145 (1986)) and the method of Evans et al. (Biochem. Biophys. Acta, 840, 43–50 (1985)).

Lungs were excised from Hartley guinea pigs (body weight: 330 g). The lungs were homogenized in phosphoric acid buffer (50 mM, pH 7.4, containing 1 mM ethylenediaminetetraacetic acid (EDTA) and 1 mM dithiothreitol (DTT)) having weight three times that of the lungs under ice-cooling. The homogenate was centrifuged at low speed (800×g) for 20 minutes, centrifuged at high speed (10,000× g) for 20 minutes and ultracentrifuged (100,000×g) for 60 minutes to give a supernatant. The supernatant was brought to 40% saturation by adding a saturated aqueous ammonium sulfate solution (pH 7.0–7.2, containing 1 mM DTT) dropwise under ice-cooling and centrifuged at high speed (10,000×g) for 20 minutes. The resulting supernatant was brought to 70% saturation by adding a saturated aqueous ammonium sulfate solution (pH 7.0–7.2, containing 1 mM DTT) dropwise and centrifuged at high speed (10,000×g) for 20 minutes. The obtained pellet was dissolved in 2 ml of Tris-acetic acid buffer (20 mM, pH 7.8, containing 1 mM DTT) and dialyzed in 2 liters of the solution to give the enzyme preparation.

$LTA_4$ used, which is the substrate, was prepared by hydrolyzing $LTA_4$ methyl ester and dissolved in ethanol.

In order to examine effects of the present compounds on the enzyme preparation, reactions were performed under the following condition using mixed solutions consisting of the composition shown in Table 1.

TABLE 1

| | |
|---|---|
| HEPES buffer | 50 mM, pH 7.8 |
| Enzyme preparation | 0.4–0.6 mg protein |
| $LTA_4$ | 63 μM |
| Aqueous DTT solution | 3 mM |
| Test compound | $10^{-2}$–$10^{-3}$ M |

The above-mentioned solution (50 μl) was incubated at 37° C. for one minute. To the reaction mixture was added 100 μl of a mixed liquid of acetonitrile-ethanol-acetic acid (150:50:3, volume ratio) under ice-cooling. The mixture was allowed to stand at −20° C. for 30 minutes and centrifuged at high speed (10,000×g) for five minutes to give a supernatant. An amount of $LTB_4$ produced in the supernatant was measured by high-speed liquid chromatography.

The degree of the inhibitory effect of each test compound on $LTA_4$ hydrolase is expressed by the inhibition rate calculated by the following equation.

$$\text{Inhibition rate (\%)} = \frac{A-B}{A} \times 100$$

Results

As examples of the experimental results, Table 2 shows concentrations of compound Nos. 3-1, 3-3, 3-9, 3-19, 3-21, 3-22, 3-23, 3-24, 3-26, 3-27, 3-28 and 8-1 required to inhibit $LTA_4$ hydrolase by 50%, i.e., $IC_{50}$.

TABLE 2

| | $IC_{50}$ (M) |
|---|---|
| Compound No. 3-1 | $2.4 \times 10^{-7}$ |
| Compound No. 3-3 | $4.7 \times 10^{-7}$ |
| Compound No. 3-9 | $9.0 \times 10^{-7}$ |
| Compound No. 3-19 | $5.6 \times 10^{-6}$ |
| Compound No. 3-21 | $1.5 \times 10^{-6}$ |
| Compound No. 3-22 | $4.0 \times 10^{-7}$ |
| Compound No. 3-23 | $2.9 \times 10^{-7}$ |
| Compound No. 3-24 | $1.1 \times 10^{-6}$ |
| Compound No. 3-26 | $5.0 \times 10^{-7}$ |
| Compound No. 3-27 | $3.8 \times 10^{-6}$ |
| Compound No. 3-28 | $7.4 \times 10^{-6}$ |
| Compound No. 8-1 | $5.9 \times 10^{-7}$ |

As shown in Table 2, the present compounds were found to inhibit the $LTA_4$ hydrolase activity remarkably at the low concentrations.

Since the above-mentioned pharmacological test shows that the present compounds have the excellent inhibitory effects on $LTA_4$ hydrolase, the compounds are expected to be excellent medicines, in particular, therapeutic agents for inflammatory diseases such as rheumatic diseases, psoriasis, inflammatory intestinal diseases, gout and cystic fibrosis, in which $LTB_4$ is concerned.

INDUSTRIAL APPLICABILITY

The present invention provides novel amino acid derivatives containing sulfur or oxygen and having an N,N-dialkylaminophenyl group at their side chain which have inhibitory effects on $LTA_4$ hydrolase and are useful as medicines, in particular, therapeutic agents for inflammatory diseases such as rheumatic diseases, psoriasis, inflammatory intestinal diseases, gout and cystic fibrosis, in which $LTB_4$ is concerned.

We claim:

1. A compound represented by the formula (I) or a salt thereof,

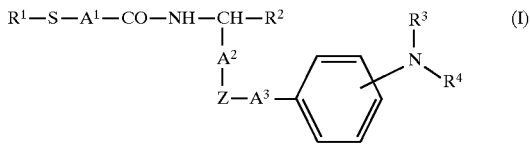

wherein $R^1$ represents a hydrogen atom, a lower alkyl group, a phenyl-lower alkyl group, a lower alkanoyl group or a benzoyl group, and each phenyl ring in the phenyl-lower alkyl group and the benzoyl group is unsubstituted or substituted by a halogen atom, a lower alkyl group or a lower alkoxy group;

$R^2$ represents a carboxyl group or a carboxyl group which is converted into an ester, an amide or a hydroxamic acid;

$R^3$ represents a lower alkyl group;

$R^4$ represents a lower alkyl group;

$A^1$ represents a lower alkylene group which is unsubstituted or substituted by a phenyl group, and the phenyl group is unsubstituted or substituted by a halogen atom, a lower alkyl group or a lower alkoxy group;

$A^2$ represents a lower alkylene group;

$A^3$ represents a lower alkylene group; and

Z represents a sulfur atom or an oxygen atom.

2. A compound represented by the formula (I) or a salt thereof,

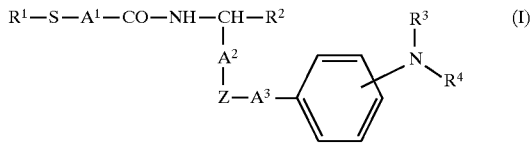

wherein $R^1$ represents a hydrogen atom, a lower alkyl group, a phenyl-lower alkyl group, a lower alkanoyl group or a benzoyl group, and each phenyl ring in the phenyl-lower alkyl group and the benzoyl group is unsubstituted or substituted by a halogen atom, a lower alkyl group or a lower alkoxy group;

$R^2$ represents a carboxyl group; a carboxyl group which is converted into a lower alkyl ester or a phenyl-lower alkyl ester; a carboxyl group which is converted into an amide with ammonia, a lower alkyl amine or a phenyl-lower alkyl amine; or a carboxyl group which is converted into a hydroxamic acid, and each phenyl ring in the phenyl-lower alkyl ester and the phenyl-lower alkyl amine is unsubstituted or substituted by a halogen atom, a lower alkyl group, a hydroxyl group, a lower alkoxy group, a lower alkylenedioxy group, a nitro group, an amino group, a lower alkylamino group or a lower alkanoylamino group;

$R^3$ represents a lower alkyl group;

$R^4$ represents a lower alkyl group;

$A^1$ represents a lower alkylene group which is unsubstituted or substituted by a phenyl group, and the phenyl group is unsubstituted or substituted by a halogen atom, a lower alkyl group or a lower alkoxy group;

$A^2$ represents a lower alkylene group;

$A^3$ represents a lower alkylene group; and

Z represents a sulfur atom or an oxygen atom.

3. A compound represented by the formula (I) or a salt thereof,

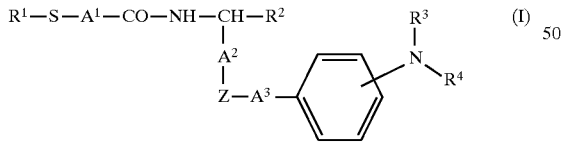

wherein $R^1$ represents hydrogen atom, a lower alkyl group, a phenyl-lower alkyl group or a benzoyl group;

$R^2$ represents a carboxyl group; a carboxyl group which is converted into a lower alkyl ester or a phenyl-lower alkyl ester; or a carboxyl group which is converted into an amide with a lower alkyl amine or a phenyl-lower alkyl amine;

$R^3$ represents a lower alkyl group;

$R^4$ represents a lower alkyl group;

$A^1$ represents a lower alkylene group which is unsubstituted or substituted by a phenyl group;

$A^2$ represents a lower alkylene group;

$A^3$ represents a lower alkylene group; and

Z represents a sulfur atom or an oxygen atom.

4. A compound represented by the formula (I) or a salt thereof,

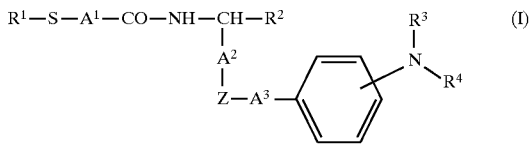

wherein $R^1$ represents a hydrogen atom, a lower alkyl group, a phenyl-lower alkyl group or a benzoyl group;

$R^2$ represents a carboxyl group; a carboxyl group which is converted into a lower alkyl ester; or a carboxyl group which is converted into an amide with a lower alkyl amine;

$R^3$ represents a lower alkyl group;

$R^4$ represents a lower alkyl group;

$A^1$ represents a lower alkylene group which is unsubstituted or substituted by a phenyl group;

$A^2$ represents a lower alkylene group;

$A^3$ represents a lower alkylene group; and

Z represents a sulfur atom or an oxygen atom.

5. The compound or a salt thereof as claimed in claim 4, wherein $R^1$ represents a hydrogen atom, a methyl group, a benzyl group or a benzoyl group;

$R^2$ represents a carboxyl group; a carboxyl group which is converted into an ethyl ester; or a carboxyl group which is converted into an amide with methylamine;

$R^3$ represents a methyl group or an ethyl group;

$R^4$ represents a methyl group or an ethyl group;

$A^1$ represents a methylene group, a methylmethylene group, an ethylene group, a propylene group, an ethylethylene group, a propylethylene group, an isopropylethylene group, a benzylethylene group, a phenetylethylene group, a trimethylene group or a methyltrimethylene group;

$A^2$ represents a methylene group or an ethylene group; and $A^3$ represents a methylene group.

6. A compound represented by the formula (I) or a salt thereof,

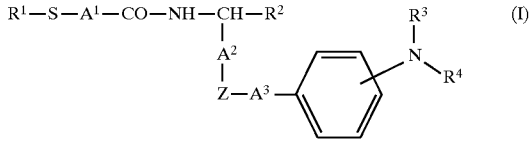

wherein $R^1$ represents a hydrogen atom;

$R^2$ represents a carboxyl group or a carboxyl group which is converted into a lower alkyl ester;

$R^3$ represents a lower alkyl group;

$R^4$ represents a lower alkyl group;

$A^1$ represents a lower alkylene group which is unsubstituted or substituted by a phenyl group;

$A^2$ represents a lower alkylene group;

$A^3$ represents a lower alkylene group; and

7. The compound or a salt thereof as claimed in claim 6, wherein $R^2$ represents a carboxyl group or a carboxyl group which is converted into an ethyl ester; $R^3$ represents a methyl group or an ethyl group; $R^4$ represents a methyl group or an ethyl group; $A^1$ represents a methylene group, an ethylene group, a propylene group, an ethylethylene group, a propylethylene group, an isopropylethylene group or a phenetylethylene group; $A^2$ represents a methylene group; and $A^3$ represents a methylene group.

8. The compound or a salt thereof as claimed in claim 2, wherein $R^1$ represents a hydrogen atom, a lower alkyl group, a phenyl-lower alkyl group or a benzoyl group.

9. The compound or a salt thereof as claimed in claim 2, wherein $R^1$ represents a hydrogen atom, a methyl group, a benzyl group or a benzoyl group.

10. The compound or a salt thereof as claimed in claim 2, wherein $R^1$ represents a hydrogen atom.

11. The compound or a salt thereof as claimed in claim 2, wherein $R^2$ represents a carboxyl group; a carboxyl group which is converted into a lower alkyl ester or a phenyl-lower alkyl ester; or a carboxyl group which is converted into an amide with a lower alkylamine or a phenyl-lower alkylamine.

12. The compound or a salt thereof as claimed in claim 2, wherein $R^2$ represents a carboxyl group; a carboxyl group which is converted into a lower alkyl ester; or a carboxyl group which is converted into an amide with a lower alkylamine.

13. The compound or a salt thereof as claimed in claim 2, wherein $R^2$ represents a carboxyl group; a carboxyl group which is converted into an ethyl ester; or a carboxyl group which is converted into an amide with methylamine.

14. The compound or a salt thereof as claimed in claim 2, wherein $R^2$ represents a carboxyl group or a carboxyl group which is converted into a lower alkyl ester.

15. The compound or a salt thereof as claimed in claim 2, wherein $R^2$ represents a carboxyl group or a carboxyl group which is converted into an ethyl ester.

16. The compound or a salt thereof as claimed in claim 2, wherein $R^3$ represents a methyl group or an ethyl group.

17. The compound or a salt thereof as claimed in claim 2, wherein $R^4$ represents a methyl group or an ethyl group.

18. The compound or a salt thereof as claimed in claim 2, wherein $A^1$ represents a lower alkylene group which is unsubstituted or substituted by a phenyl group.

19. The compound or a salt thereof as claimed in claim 2, wherein $A^1$ represents a methylene group, a methylmethylene group, an ethylene group, a propylene group, an ethylethylene group, a propylethylene group, an isopropylethylene group, a benzylethylene group, a phenetylethylene group, a trimethylene group or a methyltrimethylene group.

20. The compound or a salt thereof as claimed in claim 2, wherein $A^1$ represents a methylene group, an ethylene group, a propylene group, an ethylethylene group, a propylethylene group, an isopropylethylene group or a phenetylethylene group.

21. The compound or a salt thereof as claimed in claim 2, wherein Z represents a sulfur atom.

22. The compound or a salt thereof as claimed in claim 2, wherein $R^1$ represents a hydrogen atom, a lower alkyl group, a phenyl-lower alkyl group or a benzoyl group; and $R^2$ represents a carboxyl group; a carboxyl group which is converted into a lower alkyl ester or a phenyl-lower alkyl ester; or a carboxyl group which is converted into an amide with a lower alkylamine or a phenyl-lower alkylamine.

23. The compound or a salt thereof as claimed in claim 2, wherein $R^1$ represents a hydrogen atom, a lower alkyl group, a phenyl-lower alkyl group or a benzoyl group; and $R^2$ represents a carboxyl group or a carboxyl group which is converted into an amide with a lower alkylamine.

24. The compound or a salt thereof as claimed in claim 2, wherein $R^1$ represents a hydrogen atom, a methyl group, a benzyl group or a benzoyl group; and $R^2$ represents a carboxyl group or a carboxyl group which is converted into an amide with methylamine.

25. The compound or a salt thereof as claimed in claim 2, wherein $R^1$ represents a hydrogen atom; $R^2$ represents a carboxyl group or a carboxyl group which is converted into a lower alkyl ester; and Z represents a sulfur atom.

26. The compound or a salt thereof as claimed in claim 2, wherein $R^1$ represents a hydrogen atom; $R^2$ represents a carboxyl group or a carboxyl group which is converted into an ethyl ester; and Z represents a sulfur atom.

27. 3-[4-(N,N-Dimethylamino)benzylthio]-2-(3-mercapto-2-methylpropionylamino)propionic acid or a salt thereof.

28. (2R)-3-[4-(N,N-Dimethylamino)benzylthio]-2-((2S)-3-mercapto-2-methylpropionylamino]propionic acid or a salt thereof.

29. (2R)-3-[4-(N,N-Dimethylamino)benzylthio]-2-[(2S)-3-mercapto-2-propylproplonylamino]propionic acid or a salt thereof.

30. A pharmaceutical composition comprising a pharmaceutically effective amount of the compound or a salt thereof as claimed in claim 1 as an active ingredient in combination with a pharmaceutically acceptable carrier.

31. A leukotriene $A_4$ inhibitor comprising a pharmaceutically effective amount of the compound or a salt thereof as claimed in claim 1 as an active ingredient in combination with a pharmaceutically acceptable carrier.

32. A therapeutic agent for inflammatory diseases comprising a pharmaceutically effective amount of the compound or a salt thereof as claimed in claim 1 as an active ingredient in combination with a pharmaceutically acceptable carrier.

33. An antirheumatic agent comprising a pharmaceutically effective amount of the compound or a salt thereof as claimed in claim 1 as an active ingredient in combination with a pharmaceutically acceptable carrier.

* * * * *